(12) United States Patent
Wassell

(10) Patent No.: US 9,107,429 B2
(45) Date of Patent: Aug. 18, 2015

(54) EMULSIFIER COMPOSITION FOR SHORTENING

(75) Inventor: Paul Wassell, Bexhill-on-Sea (GB)

(73) Assignee: DUPONT NUTRITION BIOSCIENCES APS, Copenhagen (DK)

( * ) Notice: Subject to any disclaimer, the term of this patent is extended or adjusted under 35 U.S.C. 154(b) by 2090 days.

(21) Appl. No.: 10/592,549

(22) PCT Filed: Mar. 18, 2005

(86) PCT No.: PCT/GB2005/001041
§ 371 (c)(1),
(2), (4) Date: Apr. 11, 2007

(87) PCT Pub. No.: WO2005/089564
PCT Pub. Date: Sep. 29, 2005

(65) Prior Publication Data
US 2007/0207133 A1 Sep. 6, 2007

(30) Foreign Application Priority Data

Mar. 19, 2004 (GB) .................................. 0406228.7
Mar. 19, 2004 (GB) .................................. 0406229.5

(51) Int. Cl.
*A23D 7/005* (2006.01)
*A61K 35/00* (2006.01)
*A23L 1/30* (2006.01)

(52) U.S. Cl.
CPC ............. *A23D 7/0053* (2013.01); *A23L 1/3014* (2013.01); *A23V 2200/3204* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 5,698,246 A | 12/1997 | Villamar | |
| 6,060,050 A * | 5/2000 | Brown et al. | 424/93.3 |
| 6,251,478 B1 * | 6/2001 | Pacifico et al. | 427/213.3 |
| 2001/0036453 A1 | 11/2001 | Reid | |
| 2002/0044990 A1 * | 4/2002 | De Simone | 426/61 |
| 2002/0061292 A1 | 5/2002 | De Simone | |

FOREIGN PATENT DOCUMENTS

| | | | | |
|---|---|---|---|---|
| AU | WO 2005/030229 | * | 4/2005 | ............. A61K 35/74 |
| EP | 0 376 407 A1 | | 7/1990 | |
| EP | 0 666 031 A2 | | 8/1995 | |
| EP | 0 704 164 A2 | | 10/1997 | |
| EP | 0 948 896 A1 | | 10/1999 | |
| EP | 0 841 856 B1 | | 1/2000 | |
| EP | 1 010 372 A2 | | 6/2000 | |
| FR | 2 776 167 | | 9/1999 | |
| GB | 2 207 849 A | | 2/1989 | |
| JP | 62 058971 A | | 3/1987 | |
| JP | S62-058971 | | 3/1987 | |
| JP | 62 232334 A | | 10/1987 | |
| JP | 64-077122 | | 3/1989 | |
| JP | 01 228456 | | 9/1989 | |
| JP | 2000-175615 | | 6/2000 | |
| JP | 2003-500451 | | 12/2000 | |
| WO | WO 99/09839 | | 3/1999 | |
| WO | WO00/72855 | | 12/2000 | |
| WO | WO 01/15985 A1 | | 3/2001 | |
| WO | WO 01/91569 A1 | | 6/2001 | |
| WO | WO 02/00035 A1 | | 1/2002 | |
| WO | WO 02/05652 A1 | | 1/2002 | |
| WO | 2004/028460 | | 4/2004 | |

OTHER PUBLICATIONS

Krasaekoopt et al. "Evaluation of encapsulation techniques of probiotics for yoghurt" International Dairy Journal 13 (2003) 3-13.*
Beadle et al. "Composition of Corn Oil" The Journal of the American Oil Chemists' Society vol. 42, 1965 pp. 90-95.*
"Monoglyceride." Merriam-Webster Online Dictionary. 2010. Merriam-Webster Online. Feb. 19. 2010, 2pgs <http://www.merriam-webster.com/dictionary/monoglyceride>.*
"Triglycerides." Merriam-Webster Online Dictionary. 2010. Merriam-Webster Online. Feb. 19, 2010, 2pgs <http://www.merriam-webster.com/dictionary/triglycerides>.*
Britannica Online Encyclopedia "Triglyceride (chemical compound)" 2014. Web. Jul. 15, 2014 1pg <http://w w w .britannica.com/EBchecked/topic/605207/triglyceride>.*
MedicineNet.com "Definition of Triglycerides" www.medterms.com, 2 pages, accessed Jul. 15, 2014.*
Olszewska et al. "Cell Viability of *Bifidobacterium lactis* Strain in Long-Term Storage Butter Assessed with the Plate Count and Fluorescence Techniques" Czech J. Food Sci. vol. 30, 2012, No. 5: 421-428.*
Encyclopedia of Food Technology, A H Johnson & M S Peterson (eds), The Market Milk Industry, Avi Publishing Company, Westport, CT, (1974) pp. 382-684.
Danisco Cultor, Peanut Butter Stabilisers, Technical Memorandum TM 1524-1e.
Hasenhuettl GL & Hartel RW, "Food Emulsifiers & Their Applications," Springer, 1st Edition (1997) pp. 1-9.
Oxford English Dictionary (1989) pp. 396-397.
Random House Dictionary for the English Language Unabridged Edition Random House New York (1969) p. 1060.
United States Court of International Trade, *Best Foods* v. *U.S. Government*, Upon cross-motions as to classification of Reduced Fat Skippy®, (Jul. 9, 2004), Slip Op. 04-82.
Danisco Cultor, Peanut Butter Stabilisers, Technical Memorandum TM 1524-1e.

* cited by examiner

Primary Examiner — Thane Underdahl
(74) *Attorney, Agent, or Firm* — Steptoe & Johnson LLP

(57) ABSTRACT

A method of producing a water-in-oil product is described. The method comprises the step of: admixing a hydrophobic component with a water-in-oil emulsion to form said water-in-oil product, wherein said hydrophobic component comprises a probiotic in a hydrophobic medium.

22 Claims, 1 Drawing Sheet

EMULSIFIER COMPOSITION FOR SHORTENING

CLAIM OF PRIORITY

Figure 1:
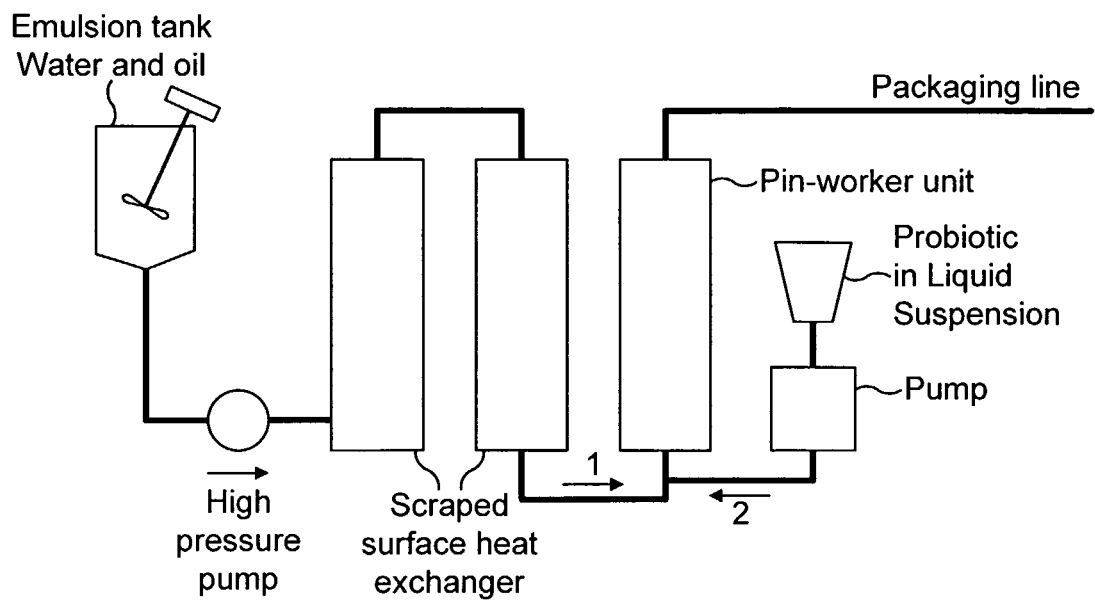

This application claims priority under 35 USC 371 to International Application No. PCT/GB2005/001041, filed on Mar. 18, 2005, which claims priority to British Patent Application No. 0406228.7, filed on Mar. 19, 2004, and British Patent Application Serial No. 0406229.5, filed on Mar. 19, 2004, each of which is incorporated by reference in its entirety.

FIELD OF INVENTION

The present invention relates to a method of producing a probiotic product capable of imparting a nutritional and/or health benefit on the consumer. The present invention also relates to use of the probiotic products. The term "product" as used herein is interchangeable with the term "preparation". Preferably the probiotic product is a water-in-oil product. Water-in-oil products are sometimes referred to as water-in-fat products.

INTRODUCTION

A growing awareness of the relationship between diet and health has resulted in an increased demand for food products that are capable of enhancing the health as well as provide basic nutrition. Examples of such food products include probiotics.

The term probiotic, meaning "for-life", is derived from Greek which already indicates the most essential properties of probiotic cultures. The term probiotic was first used by Lilly and Stillwell, 1965 to describe "substances secreted by one micro-organism which stimulate the growth of another" and thus contrasted by the term antibiotic (Lilly and Stillwell, 1965 *Science* 147: 747-748). It may be because of this positive and general claim of the definition that the term probiotic was subsequently applied to other subjects and gained a more general meaning. Now the definition of the term refers to "viable bacteria that beneficially influence the health of the host".

Different studies have demonstrated that the average human and animal gut contains about 100 different species of bacteria, including 'probiotic' bacteria, such as for example bacteria belonging to the genera *Lactococcus, Streptococcus, Pediococcus, Enterococcus, Leuconostoc, Carnobacterium, Propionibacterium, Lactobacillus* and *Bifidobacterium*.

Regular consumption of 'probiotic' bacteria have been reported to enhance gastrointestinal tract function and stability, improve protection against infection and carcinogenic mutagens, bolster the immune system, alleviate lacetic acid intolerance, improve digestion and nutrient absorption, reduce blood cholesterol and reduce risks to allergies and wheat intolerance.

The bacteria *Bifidobacterium* were discovered in the year 1899 in the faeces of breast-fed infants. This was of particularly interest as these bacteria are often the most abundant in bread-fed infants and regarded as the primary reason for their enhanced general resistance to disease.

It is known that bifidobacteria play a key role in the intestinal microflora of humans and animals throughout their life. Crohn's disease patients often have a considerably lower number of bifidobacteria in their stools than healthy individuals. Children usually have a large quantity of bifidobacteria in their stool than adults and, therefore, have a lower stool pH, which has been implicated as the reason for lower capacity for establishment of pathogenic micro-organisms.

Probiotic bacterial cultures are today found in a wide rage of products for consumption such as dairy products and different emulsions such as oil-in-water products and water-in-oil products.

Incorporation of probiotics into such formulations is particularly fraught with difficulties, because of the very harsh processing conditions.

Typically, the probiotic culture is incorporated into the oil-in-water spread via a water phase, which is possibly pre-pasteurised, alongside other water phase components.

When preparing water-in-oil products the probiotic micro-organisms are introduced into the oil phase which when subjected to deep cooling and scrapping actions within for example a tubular Scraped Surface Heat Exchanger (SSHE) are damaged and have significantly reduced viability.

A particular approach to maintain the viability and the survival rate of probiotic micro-organisms is to generate an appropriate water droplet size during processing.

However, this approach can lead to the development of processes that are capable of working within very narrow margins that can limit the viability of the probiotic micro-organisms and ultimately lead to significantly reduced shelf life of the end water-in-oil product.

EP 0 376 407 discloses a water-in-oil spread comprising lacetic acid bacteria. The lacetic acid bacteria together with the other ingredients for making the spread are heated to 50° C. with stirring in a SSHE to form the emulsion.

EP 1 010 372 discloses functional food/health food in the form of a baked good comprising a non-baked fat-based composition and a baked part. Lacetic acid bacteria are mixed together with the other ingredients of the fat based composition without heating above 40° C.

EP 0 948 896 discloses a method of preparing a water-in-oil emulsion. A liquid fat phase, an aqueous phase, flavour and probiotic micro-organisms are mixed together and treated in a votator type scraped heat exchanger until a homogenous water-in-oil emulsion is obtained.

There accordingly exists a need for a method of producing a probiotic product, such as a water-in-oil product, in which damage to the probiotic micro-organisms is limited whilst providing wider margins for the formation of the dispersion (such as, for example, a water-in-oil emulsion).

Broad Aspects

The terms "water-in-oil product" and "water-in-oil emulsion" as used herein provide an example of a probiotic product and dispersion, respectively. However, the skilled person would appreciate that the present invention covers other probiotic products formed by admixing a dispersion with an inert hydrophobic component, wherein the hydrophobic component comprises a viable probiotic micro-organism in a hydrophobic medium.

In a broad aspect, the present invention relates to a method of forming a water-in-oil preparation (sometimes referred to as a "water-in-oil composition" or "water-in-oil product"), said method comprising admixing a hydrophobic component (sometimes referred to as a "hydrophobic combination" or in some instances "combination") with a water-in-oil emulsion, wherein the hydrophobic component comprises a viable probiotic micro-organism in a hydrophobic medium. The viable probiotic micro-organism imparts nutritional and/or health benefits to the consumer.

The present invention also relates to a method of producing a water-in-oil product; wherein said water-in-oil product comprises a water-in-oil emulsion and a hydrophobic component; wherein said water-in-oil emulsion is formed separately from the hydrophobic component; and wherein the hydrophobic component is added to said water-in-oil emulsion after the water-in-oil emulsion is formed.

The present invention further relates to a water-in-oil product comprising a hydrophobic component that is prepared in situ by mixing a viable lacetic acid micro-organism in a suitable continuous oil phase.

The present invention also relates to a method for forming a water-in-oil product so as to provide a preparation that comprises a viable lacetic acid micro-organism which is capable of imparting nutritional and/or health benefits on the consumer.

The present invention further relates to method of preparing a probiotic product comprising admixing a dispersion with an inert hydrophobic component, wherein said hydrophobic component comprises a probiotic in a hydrophobic medium, such that the probiotic is kept discrete from said dispersion in the admixed product. The term "discrete" means that contact of the probiotic with the dispersion is kept separate or is restricted. Without wishing to be bound by theory, the probiotic is encapsulated by a thin film of hydrophobic medium which separates/restricts the contact of the probiotic with the dispersion.

The present invention further relates to a product comprising peanut butter and a probiotic.

The present invention also relates to products produced by a method herein.

In particular there is provided a water-in-oil preparation which on the day of production comprises about $10^8$-$10^9$ cfu/g (colony forming units/gram of product) and wherein about $10^4$-$10^8$ cfu/g lacetic acid micro-organisms remain viable about 12 weeks after the day of production.

To date no one has suggested admixing a probiotic in a hydrophobic medium with a pre-formed dispersion such as a water-in-oil emulsion. The method of the present invention avoids the damage to a probiotic that occurs during the formation of a dispersion. It further allows wider parameters to be used in the formation of the dispersion without reducing the shelf life of the probiotic product through damage to the probiotic. Furthermore, the method of the present invention substantially prevents rehydration of the probiotic in the probiotic product. The term "dispersion" as used herein refers to a system comprising a gas, liquid or colloid in which particles are dispersed.

The probiotic product of the present invention is capable of imparting nutritional and/or health benefits on the consumer.

Preferably, the present invention relates to a water-in-oil composition suitable for forming a water-in-oil product comprising viable lacetic acid micro-organisms which have been introduced to the water-in-oil emulsion by a hydrophobic combination which comprises a viable lacetic acid micro-organism in a continuous oil phase.

Other aspects of the present invention are presented in the accompanying claims and in the following description. These aspects are presented under separate section headings. However, it is to be understood that the teachings under each section are not necessarily limited to the particular section heading.

Specific Aspects

One aspect of the present invention relates to a method for producing a water-in-oil product, said method comprising the step of: admixing a hydrophobic component with a water-in-oil emulsion to form said water-in-oil product, wherein said hydrophobic component comprises a probiotic in a hydrophobic medium.

In another aspect of the present invention the probiotic comprises a viable micro-organism selected from the group consisting of: *Lactococcus, Streptococcus, Pediococcus, Enterococcus, Leuconostoc, Carnobacterium, Propionibacterium, Lactobacillus* and *Bifidobacterium*. Preferably the micro-organism is a *Bifidobacterium* and/or *Lactobacillus*. More preferably the micro-organism is species *Bifidobacterium* sp. 420 and/or *Lactobacillus acidophilus*.

In one aspect of the present invention the hydrophobic component comprises a probiotic in a hydrophobic medium. Preferably the hydrophobic medium is an oil phase, more preferably a continuous oil phase. More preferably the hydrophobic medium comprises a continuous oil phase comprising an unsaturated liquid oil and triglyceride, preferably wherein the triglyceride also comprises a monoester.

In one aspect of the present invention the hydrophobic component comprises a probiotic in a hydrophobic medium, wherein the probiotic is added to the hydrophobic medium in dry form, preferably in powder form.

In a further aspect of the present invention there is provided a method of producing a water-in-oil product, said method comprising admixing a hydrophobic component with a water-in-oil emulsion; wherein the water-in-oil product is not subjected to physical manipulations that are capable of causing cell damage.

In a yet another aspect of the present invention there is provided a method of producing a water-in-oil product, said method comprising admixing hydrophobic component a hydrophobic component with a water-in-oil emulsion; wherein the water-in-oil product further comprises a prebiotic.

In a further aspect of the present invention there is provided a method of preparing a probiotic product comprising: admixing a dispersion with an inert hydrophobic component; wherein said hydrophobic component comprises a probiotic in a hydrophobic medium, such that the probiotic is kept discrete from said emulsion or dispersion in the admixed product.

In another aspect of the present invention the dispersion is an emulsion, preferably a water-in-oil emulsion.

In a further aspect of the present invention the probiotic product is peanut butter.

In another aspect of the present invention there is provided products produced by a method according to the present invention.

In a further aspect of the present invention there is provided a product obtained by the use of a product produced by a method according to the present invention.

In one aspect, the present invention provides a product produced by a method according to the present invention or a subsequent product when packaged.

In one aspect, the present invention provides a product comprising peanut butter and a probiotic.

In another aspect, the present invention relates to a water-in-oil emulsion suitable for forming a water-in-oil product with a hydrophobic component, wherein said component comprises a viable lacetic acid micro-organism in a continuous oil phase.

In another aspect, the present invention relates to a use of a water-in-oil emulsion to form a water-in-oil product with a hydrophobic component, wherein said component comprises a viable lacetic acid micro-organism in a continuous oil phase.

In a further aspect, the present invention relates to a water-in-oil composition comprising a hydrophobic combination that is prepared in situ by mixing a viable lacetic acid micro-organism in a suitable continuous fat phase. A suitable continuous fat phase comprises unsaturated liquid oil and triglyceride where the triglyceride also comprises a monoester.

Preferably the liquid oil comprises in the range of from about 95%-98% unsaturated liquid oil and the triglyceride comprises in the range of from about 2%-5% where the monoester component comprises at least 10% of the triglyceride. Preferably the triglyceride has an iodine value of from 2 to 35.

In a further aspect, the present invention also relates to a water-in-oil preparation comprising a water-in-oil emulsion and a hydrophobic combination wherein said hydrophobic combination comprises a viable lacetic acid micro-organism in a continuous oil phase, where said product comprises from $10^4$-$10^8$ cfu/g of viable lacetic acid micro-organism about 12 weeks after the day of production.

In another aspect the present invention relates to a method of producing a water-in-oil preparation the method comprising the steps of forming a water-in-oil emulsion, adding a hydrophobic combination which comprises a viable lacetic acid bacterium, mixing the emulsion with the hydrophobic combination; wherein the hydrophobic combination is added to the water-in-oil emulsion after the emulsion has been formed; and wherein the viable lacetic acid micro-organism imparts nutritional and/or health benefits to the consumer.

In another aspect, the present invention provides an in situ process for preparing a hydrophobic combination; the process comprising the steps of incorporating a lacetic acid bacterium in a continuous oil phase comprising unsaturated liquid oil and triglyceride so as to produce a viable lacetic acid bacterium in a continuous oil phase, wherein the triglyceride comprises a monoester.

Preferable Aspects

In a further preferred aspect the viable lacetic acid micro-organism is added to the hydrophobic combination in a powder form.

Preferably the viable lacetic acid bacterium is incorporated into the continuous oil phase in a powder form.

In another preferred aspect the viable lacetic acid micro-organism is a viable lacetic acid bacterium.

In another preferred aspect the viable lacetic acid bacterium is selected from a group consisting of *Lactococcus, Streptococcus, Pediococcus, Enterococcus, Leuconostoc, Carnobacterium, Propionibacterium, Bifidobacterium* and *Lactobacillus* genera.

In a preferred aspect of the present invention the viable lacetic acid bacterium belongs to the genus *Bifidobacterium* and/or *Lactobacillus*.

In a further preferred aspect of the invention the viable lacetic acid bacterium belongs to the species *Bifidobacterium* sp. 420. For the avoidance of doubt, the taxonomical name of *Bifidobacterium* sp. 420 is *Bifidobacterium* lactis 420. These terms are used herein interchangeably.

It is noted that species that have been taxonomically classified as *Bifidobacterium* lactis are presently under review. In particular, it is thought that some species previously classified as being *B. lactis* may, in fact, be *B. animalis*. In the present invention for some aspects it is intended to cover both *B. lactis* species which may subsequently be taxonomically re-named as *B. animalis* and vice versa. In particular, *Bifidobacterium* sp. 420 has been classified previously as *B. lactis* 420.

However, should this organism be reclassified as *B. animalis* 420 (or for that matter is reclassified as any other species of *Bifidobacterium*), it is intended that this organism is encompassed by the present invention.

In one embodiment, the microorganism according to the present invention may be *Bifidobacterium* sp. 420.

*Bifidobacterium* sp. 420 is commercially available from Danisco A/S (Denmark).

In a further preferred aspect of the invention the viable lacetic acid bacterium belongs to the species *Lactobacillus acidophilus*.

In another preferred aspect of the invention there is provided a container which comprises the hydrophobic combination of the present invention, wherein said container also has thereon a label indicating use and/or approval for use to improve the microbial balance of the gastrointestinal tract after consumption of a product containing said hydrophobic combination.

In another preferred aspect of the invention there is provided a container which comprises the water-in-oil product of the present invention, wherein said container also has thereon a label indicating use and/or approval for use to improve the microbial balance of the gastrointestinal tract after consumption of the product.

In a further preferred aspect the water-in-oil preparation which is obtained by the method described herein is not subjected to physical manipulations after the addition of the viable lacetic acid micro-organism which can cause cell damage.

In another preferred aspect the continuous oil phase of the hydrophobic combination comprises an unsaturated liquid oil and triglyceride, preferably wherein the triglyceride comprises a monoester.

In another preferred aspect the continuous oil phase comprises liquid oil in the range of from about 95%-98% and triglyceride in the range of from about 2%-5% and wherein the triglyceride also comprises at least 10% monoester.

In yet another preferred aspect the triglyceride component of the hydrophobic combination has an iodine value of from 2 to 35, wherein the iodine value is the number of grams of iodine absorbed by 100 grams of triglyceride.

In a further preferred aspect the triglyceride component of the hydrophobic combination may be fully hydrogenated and/or non-hydrogenated and/or partially hydrogenated, wherein said triglyceride is fully hydrogenated.

In a further aspect, preferably there is provided a method of forming a probiotic product comprising: admixing a dispersion with an inert hydrophobic component; wherein said hydrophobic component comprises a probiotic in a hydrophobic medium, such that the probiotic is kept discrete from said dispersion in the admixed product, wherein the probiotic product is peanut butter.

In another preferred aspect, preferably the dispersion is an emulsion, preferably a water-in-oil emulsion.

The water-in-oil emulsion may contain from about 5% to about 98% wt. fat content.

In one respect, preferably the water-in-oil emulsion comprises at least 10%, preferably at least 15%, more preferably at least 20%, more preferably at least 30% and even more preferably at least 35% wt. fat content.

In one respect, preferably the water-in-oil emulsion comprises up to 95%, preferably up to 90%, more preferably up to 75%, more preferably 65% and even more preferably up to 55% wt, fat content.

In one respect preferably the water-in-oil emulsion has about 40% fat content.

Preferably the water-in-oil product is a water-in-oil spread, a water-in-oil butter, a water-in-oil margarine or it can be any water-in-oil product that is capable of benefiting from the water-in-oil composition as described herein.

In one respect, preferably the water-in-oil product is a low-fat water-in-oil product which can be a low-fat water-in-oil spread, a low-fat water-in-oil butter, a low-fat water-in-oil margarine, or it can be any low-fat water-in-oil product that is capable of benefiting from the water-in-oil composition as described herein.

In one respect, preferably the water-in-oil product is a reduced fat water-in-oil spread, a reduced fat water-in-oil butter, a reduced fat water-in-oil margarine or it can be any reduced fat water-in-oil product that is capable of benefiting from the water-in-oil composition as described herein.

In one respect, preferably the water-in-oil product is a full fat water-in-oil spread, a full fat water-in-oil butter, a full fat water-in-oil margarine or it can be any full fat water-in-oil product that can benefit from the water-in-oil composition as described herein.

The term "spread" means edible oil spread that is spreadable food composed of edible oils and water in the form of an emulsion of the type water-in-oil. Examples of spreads include butter, margarine and low fat spreads.

The term "full fat" as used herein means a water-in-oil product characterised with a fat content of in the range of from about 63% to about 98% wt. fat content.

The term "reduced fat" as used herein means a water-in-oil product which is characterised with a fat content which is less than the fat content normally found or generally associated with its counterpart. The reduced fat product may have 1%, 2%, 3%, 4%, 5%, 10%, 15%, 20%, 30%, 40% or less than the fat content normally found or generally associated with its counterpart.

As used herein the term "low-fat" means a water-in-oil product generally characterised as having a fat content in the range of from about 5% to about 40% wt. fat content.

Preferably the low-fat water-in-oil product is characterised with less than 40%, preferably less than 39%, preferably less than 38%, preferably less than 37%, preferably less than 35%, preferably less than 30%, preferably less than 20%, preferably less than 10%, preferably about 5% wt. fat content.

In one respect, preferably the reduced fat water-in-oil product as described herein has a fat content in the range of from about 43% to about 62% wt. fat content.

In a preferred aspect the water-in-oil emulsion is capable of imparting a prebiotic effect on the consumer.

Preferably, the water-in-oil emulsion also comprises polydextrose, where the polydextrose is Litesse™, pectin and/or maltodextrose.

In one respect, preferably the present invention provides a water-in-oil preparation comprising a water-in-oil emulsion and a hydrophobic combination containing viable lacetic acid bacteria in a continuous oil phase wherein the spread is capable of imparting a probiotic effect and/or a prebiotic effect and/or a symbiotic effect on the consumer.

Advantages

Some advantages of the present invention have been discussed above. Some further advantages are presented in the following commentary.

A primary advantage of the present invention is the provision of a water-in-oil preparation that comprises a probiotic (for example lacetic acid micro-organisms) which remains viable for prolonged periods of time. This is achieved by adding to a pre-formed water-in-oil emulsion a hydrophobic component comprising a viable lacetic acid micro-organism in a hydrophobic medium (for example a continuous oil phase).

Another advantage of the present invention is that the water-in-oil composition as described herein may be used in the preparation of water-in-oil products which are characterised with different amounts of fat content. Preferably the fat content of the water-in-oil product is in the range of from about 5% to about 98%.

Another advantage of the present invention is that the hydrophobic component typically localises to the oil/fat element of the preparation; thus limiting the contact of the viable lacetic acid micro-organism with water. This particular compartmentalisation combination has the capacity to limit, prevent or diminish the re-hydration of the viable lacetic acid micro-organism—and therefore prolongs the viability of the micro-organism.

Another advantage of the present invention is that after production of the water-in-oil product the viable lacetic acid micro-organisms are in the range of from about $10^8$-$10^9$ cfu/g of the product.

Another advantage of the present invention is the provision of a water-in-oil preparation that is characterised with a potentially increased shelf life. The shelf life of the product would generally be determined by the capacity of the lacetic acid micro-organisms to exhibit viable numbers in the range of from about $10^4$-$10^6$ cfu/g. By way of example, water-in-oil product may be characterised with viable lacetic acid micro-organisms in the range of from about $10^4$-$10^8$ cfu/g approximately 12 weeks after the day of production.

Another advantage of the present invention is the separation of the process forming the water-in-oil emulsion from the process of forming the hydrophobic combination.

Another advantage of the present invention is the addition of the hydrophobic combination to the pre-formed water-in-oil emulsion before mixing and optionally packaging of the water-in-oil product.

Advantageously the viable lacetic acid micro-organism of the hydrophobic combination can be any micro-organism which is capable of imparting nutritional and/or health benefits on the consumer.

In another advantage of the present invention the water-in-oil preparation may also comprise a water-in-oil emulsion which is supplemented with prebiotic supplements such as polydextrose (i.e. Litesse™), pectin and maltodextrin. Since polydextrose is a unique reduced-calorie (one calorie/gram) additive water-in-oil products can be formed which can be classified as reduced calories products.

Another advantage of the present invention is that the water-in-oil composition suitable for forming a water-in-oil product upon ingestion is capable of improving the microbial balance of the gastrointestinal tract after consumption.

Another advantage of the present invention is that the water-in-oil composition suitable for forming a water-in-oil product upon ingestion is capable of imparting a prebiotic effect on the consumer.

Another advantage of the present invention is that the water-in-oil composition suitable for forming a water-in-oil product upon ingestion is capable of improving the nutritional and/or the microbial balance of the gastrointestinal tract after consumption. In other words the water-in-oil product has the capacity to act as a symbiotic on the consumer.

Advantageously, where the product is a foodstuff, the viable micro-organism should remain effective through the normal "sell-by" or "expiration" date during which the food product is offered for sale by the retailer. Preferably, the effective time should extend past such dates until the end of the normal freshness period. The desired lengths of time and normal shelf-life may vary from foodstuff to foodstuff and those of ordinary skill in the art will recognise that shelf-life times will vary depending on the type of foodstuff, the size of the foodstuff preparation, storage temperatures, processing conditions, packaging material and packaging equipment.

Fat

Throughout this specification the terms oil and fat are used interchangeably.

According to the present invention oil encompasses any oil or fat that is suitable for consumption.

Thus the fat or oil of the water-in-oil preparation may be any suitable for consumption fat that is derived from plant, from dairy, from a non-dairy or synthetically generated.

The fat or the oil can be a liquid fat or oil and/or it can be a solid fat or oil.

The liquid form oil or fat may be derived from either vegetable or animal sources. Liquid vegetable oils of fats can be derived from soybean oil, sunflower oil, palm oil, palm kernel oil, both high and low erucic rapeseed oil, coconut oil, olive oil, sesame oil, peanut oil, corn oil and mixtures thereof.

Animal liquid oils or fats may be derived from fish oil, tallow, sardine oil, dairy fat and mixtures thereof.

The solid form oil or fat may include triglycerides from either vegetable or animal sources. Such vegetable triglycerides include soybean oil, sunflower oil, palm oil, palm kernel oil, both high and low erucic rapeseed oil, coconut oil, olive oil, sesame oil, peanut oil, corn oil and mixtures thereof.

Triglylcerides from animal sources include fish oil, tallow, sardine oil, dairy fat and mixtures thereof.

The dairy fat may originate from any lactating livestock animal whose milk is suitable for consumption. Examples of such livestock animals include cows, buffalo, goats, lama, sheep, horses, camels and other ruminants.

In a preferred embodiment, cows' milk fat may provide a suitable source of the dairy fat used in the practice of the invention.

"Dairy fat" as used above may be derived from cream, skimmed milk, semi-skimmed milk, full-fat milk, cultured buttermilk, buttermilk powder, skimmed milk powder, yoghurt, quark, fromage frais, whey powder and butter.

Other suitable fat source that is capable of being used for forming a water-in-oil preparation include "non-dairy fat" that may be derived from plants such as soy or rice or it can be a synthetically generated fat that is suitable for consumption.

Synthetically generated fat suitable for consumption may be chemically, physically and/or genetically modified products such as hydrogenated, fractionated and/or inter-esterified triglyceride mixtures and mixtures of two or more thereof, as well as edible substances that are physically similar to triglycerides such as waxes, e.g. jojoba oil, and poly fatty acid esters mono- or disaccharides, that can be used as replacement for or in a mixture with triglycerides.

The solid fat content can conveniently be determined by measuring the NMR N-value as described in Fette, Seifen, Anstrichmittel, 80 (1978), 180-186, which indicates the amount of fat present in the solid state expressed in percentage of the weight of the fat.

Other fats useful in the practice of the present invention are described in the Encyclopedia of Chemical Technology, Volume 8, The Interscience Encyclopedia, Inc., New York, pages 800 through 808.

The skilled person would appreciate that the fat content will have a direct affect on texture, flavour and stability of the viable lacetic acid micro-organism in the water-in-oil product.

It has been suggested that the two qualities of fat that affect these properties are the solid fat index (SFI) and the crystal structure of the fats used. It is envisaged that ordinarily the water-in-oil products as described herein may consist of at least two different fats to create the desired SFI. Using multiple fats also helps stabilise the crystalline structure and thus viability of the micro-organism in the end water-in-oil product.

Water

As already stated, the present invention relates to water-in-oil preparations which comprise a water-in-oil emulsion and a hydrophobic combination comprising a viable lacetic acid micro-organism in a continuous oil phase. The water-in-oil emulsion is formed before the hydrophobic combination comprising the viable lacetic acid micro-organism in the hydrophobic medium is added to it.

While the two substances i.e. water and oil are generally immiscible, solid fats will hold water suspended even though the mixture is not, strictly speaking, in the form of a mixture, provided however that there is a sufficient excess of solid fats to do so. Thus, in conventional water-in-oil preparations that may comprise oil in the range of for example above 45% the fat is present in a sufficient excess making the mixed product stable for all commercial purposes.

At the other extreme, however, the larger relative proportions of water in low-fat water-in-oil products that contain less than for example about 45%, destabilise the mixture unless the two are properly dispersed. In order to achieve a uniform dispersion of the fat into the water, specific equipment is employed which uses among others high pressure and scraping. Such equipment include but is not limited to a tubular Surface Heat Exchanger (SSHE) such as Votator™, or a Diacooler.

Typically, the average water droplet size of the dispersed aqueous phase is between about 1 and 60 um, but it may be larger or smaller than that. Preferably the droplet size ranges from about 1 to about 30.

The average water droplet size, as referred to herein, is the volume weighted mean of the droplet size distribution. It can be determined with NMR following the procedure as described in J. Colloid and Interface Science 140, (1990), pp. 105-113, & U.S. Pat. No. 5,302,408 herein incorporated by reference.

With such a water droplet size satisfactory flavour release in the mouth can be obtained.

Without wishing to be bound by theory, it has been suggested that the capacity of the micro-organisms to remain viable for prolonged periods of time in the probiotic product (for example a water-in-oil product) is their localisation in the immediate proximity or within the fat droplets (i.e. they are discrete). Such localisation will significantly limit or prevent rehydration of the micro-organisms, which results in a prolonged viability of the micro-organism. Preferably the lacetic acid micro-organism of the water-in-oil composition remains viable for up to 12 weeks after the day of production of the water-in-oil product.

The average droplet size can generally be varied, by adjusting the conditions during the preparation. If, for example, the spread is prepared using Votator™ equipment, then the average droplet size may be decreased, for example by increasing the shear forces exerted, e.g. by increasing the rotor speed or the number of blades, or by decreasing the annulus.

Mixing of the Water-in-Oil Emulsion

The formation of the water-in-oil emulsion of the water-in-oil composition according to the present invention includes the steps of mixing the fat and water under conditions favouring the formation of a water-in-oil phase relationship, which conditions can be readily determined with a minimum of experimentation by a person skilled in the relevant arts in light of the present disclosure.

By way of example, there is provided a process for emulsifying a mixture of water and oil, in the presence of emulsifying agents, wherein the water is heated to a temperature about equal to that of a melted fat. In addition to facilitating the desired emulsification of the mixture, the preheating of the water ensures that the thermodynamic processes entailed in the above mentioned tailoring of the fats crystal population are not unduly disrupted. The water is heated to between 32° C. and 39.5° C. (preferably 33° C. to 37° C.). Note that if the temperature of the mixture exceeds about 40° C., then not only are the benefits associated with thermal tailoring of for example the fat crystal population lost but phase inversion also can, occur, and the thermal contribution of the water to the mixture should be adjusted to take this into account.

The two components—i.e. the water and the oil or fat—are then admixed under continuous agitation, by introducing water into the oil in a manner which at no time should causes any local concentration of water sufficient to initiate phase inversion of the incipient emulsion. Slow rates of addition and sparging (high pressure) the water into the oil both assist in minimising any localisation of water at the outset of the emulsification process.

The dispersed phase can be divided and subdivided to a point approaching the limits of the indigenous and/or added, if any, emulsifying agents' ability to support the mixture (i.e. the emulsifying agents' capacity to effect the increased interfacial surface area in the manner required to continue to stabilise that interface).

By way of example in order to achieve a uniform dispersion as described above, specific equipment may be employed which uses among others high pressure. Such equipment include but is not limited to a tubular Surface Heat Exchanger (SSHE), Votator™ or a Diacooler™.

Mixing of the Peanut Butter Dispersion

In one aspect of the present invention, there is provided a peanut butter comprising a probiotic such that the peanut butter is capable of imparting a nutritional and/or health benefit on the consumer.

In another aspect of the present invention, there is provided a method of forming a probiotic product comprising: admixing a dispersion with an inert hydrophobic component; wherein said hydrophobic component comprises a probiotic in a hydrophobic medium, such that the probiotic is kept discrete from said dispersion in the admixed product, wherein the probiotic product is a peanut butter product.

The formation of such a dispersion includes the step of heating peanut butter paste and optionally adding sugar, salt, emulsifying agents and/or other components. The peanut butter is then cooled and admixed with the hydrophobic component of the present invention.

As the peanut butter cools the dispersion becomes more stable and separation of the liquid oil in the finished product is less likely. However, as the temperature decreases the viscosity of the dispersion increases making the admixing of the hydrophobic component and handling of the product during packaging more difficult. Thus, there is a balance to be achieved between viscosity and stability. Persons skilled in the art would appreciate that the temperature ranges to which the peanut butter is cooled to depends on the composition of the peanut butter, such as the emulsifiers used, and the degree of viscosity desired during packaging Preferably, the temperature at which the peanut butter and hydrophobic component are admixed is optimal for viability of the probiotic. Preferably, the temperature does not exceed 40° C., preferably the temperature does not exceed 37° C. More preferably, the temperature at which peanut butter and hydrophobic component are admixed is between 25 and 40° C., preferably between 30 and 37° C.

Hydrophobic Medium

The probiotic product formed by the method of the present invention comprises a probiotic which has been introduced to the dispersion by the hydrophobic component—i.e. the probiotic is in a hydrophobic medium.

Preferably, the hydrophobic medium is an oil phase, more preferably a continuous oil phase.

The continuous oil phase component of the probiotic composition according to the present invention is added to the pre-formed dispersion, described before and then mixed and then, optionally the probiotic preparation is packaged.

Preferably the continuous oil phase is suitable for consumption.

Preferably the continuous oil phase comprises a liquid oil and triglyceride wherein the triglyceride also comprises a monoester. Thus, the continuous oil phase into which the viable lacetic acid micro-organism is redistributed and/or resuspended comprises a liquid oil element and a solid or hard oil element.

Preferably the liquid oil element of the hydrophobic combination is derived from vegetable, animal or synthetic.

Preferably the liquid oil is polyunsaturated and/or monounsaturated.

The triglyceride element of the hydrophobic combination has an iodine value of from about 2 to about 35. Those of skill in the art would be aware that the iodine value is generally used to represent the level of saturation of fatty acids.

Preferably the triglyceride of the continuous oil phase is a fully hydrogenated triglyceride comprising a fatty acid monoester. By way of example the triglyceride and the monoester of the hydrophobic combination may be supplied by Grindsted™.

It is within the context of the present invention that the viscosity and the cell density of the continuous oil phase may be modulated depending on the use and/or the mode of application and/or the mode of administration.

As used herein the term "modulate" means to affect, to vary, to adjust, to increase, to decrease or generally to be able to regulate or modify the level of a particular component of the water-in-oil composition.

Thus, it is possible to modulate the dilution of the viable lacetic acid micro-organism in the continuous oil phase by adjusting the ratio of the micro-organism added to the triglyceride.

Alternatively or in addition the dilution of the viable lacetic acid micro-organism may be modulated by adjusting the level of saturation and unsaturation of the triglyceride.

Alternatively or in addition the dilution of the viable lacetic acid micro-organism may be modulated by adjusting the inclusion of the monoester.

Preferably the amount of liquid oil in the continuous oil phase is in the range of from about 95% to about 98%, preferably from about 95.5% to about 97.5% preferably from about 96% to about 97%. Most preferably the liquid oil is about 98%.

Preferably the amount of fully saturated or partially saturated triglyceride in the continuous oil phase of the hydrophobic combination comprises from about 1.5% to about 5%, preferably from about 2% to about 4%, preferably from about 2.5% to about 3.5%. Preferably the partially saturated or fully saturated triglyceride component of the continuous oil phase of the hydrophobic combination is about 2%. As stated above the triglyceride can be fully saturated or partially saturated.

Preferably the amount of the fatty acid monoester component of the partially saturated or fully saturated triglyceride of the continuous oil phase of the hydrophobic combination if in the range of from about 5% to about 15%. Preferably the amount of monoester is in the range of from about 6% to about 12%. Preferably from about 7% to about 10%.

Most preferably the amount of the fatty acid monoester component of the partially saturated or fully saturated triglyceride in the continuous oil phase of the hydrophobic combination is about 10%.

Preferably the hydrophobic component has a water activity ($a_w$) of less than 0.2 whereby the water activity is a measure of water content equivalent to percent humidity divided by 100.

In Situ Preparation of the Combination

According to one of the aspects of the present invention, the hydrophobic combination containing the viable lacetic acid micro-organism in a continuous oil phase is produced in situ.

The continuous oil phase is formed by firstly heating the liquid oil and the triglyceride which comprise a monoester to at least about 10° C. above the melting temperature of the triglyceride and the monoester. Initially one part of triglyceride and five parts of liquid oil are heated to a temperature in the range of from about 70° C. to about 85° C. Preferably to a temperature of from about 72° C. to about 82° C. Preferably of from about 75° C. to about 80° C. Preferably the temperature at which the liquid oil and the hard form are melted is about 80° C. After complete melting of the triglyceride is achieved the balance of the liquid oil is added to the continuous oil phase.

Without wishing to be bound by theory, upon cooling of the melted continuous oil phase a crystal type network is formed at ambient temperature. At this stage the lyophilised or spray dried or freeze dried viable lacetic acid micro-organism culture is added to the continuous oil phase which is mixed gently to homogeneity. In order to obtain a homogeneous suspension of viable lacetic acid micro-organisms in the continuous oil phase the crystal structure is gradually disrupted in order to form a continuous oil phase comprising an evenly distributed viable lacetic acid micro-organisms.

Preferably the temperature of the cooled continuous oil phase does not adversely affect the viability of the lacetic acid micro-organism.

Preferably the mixing of the viable lacetic acid organism and the continuous oil phase does not involve vigorous physical manipulations which may damage or otherwise impair the viability of the lacetic acid micro-organism.

The so formed hydrophobic combination which comprises the viable lacetic acid micro-organism in a continuous oil phase can be packaged and stored for later use.

Alternatively the hydrophobic combination can be added to the pre-formed water-in-oil suspension in order to generate a water-in-oil product as described herein.

Preparation of the Probiotic Product

The water-in-oil emulsion is used herein as an example of a dispersion. However, the skilled person will appreciate that other dispersions may be used interchangeably with the water-in-oil emulsion.

Preferably the mixing of the hydrophobic component and the water-in-oil emulsion does not involve vigorous manipulations which may damage or otherwise impair the viability of the probiotic.

Preferably the hydrophobic component and water-in-oil emulsion are admixed to homogenicity. Preferably the duration and strength of shear forces applied admixing the water-in-oil emulsion and hydrophobic component are minimised.

Preferably the rate of stirring is greater than about 50 rpm, more preferably between 50 and 1000 rpm, more preferably about 100 rpm.

Preferably the temperature at which the water-in-oil emulsion and hydrophobic component are mixed is optimal for viability of the probiotic. Preferably the temperature does not exceed about 40° C., preferably the temperature is between 5 and 40° C., more preferably between 10 to 25° C.

Micro-Organism

The term "micro-organism" encompasses micro-organisms and means a microscopic organism which may be unicellular or multi-cellular which is capable of normal growth and development.

A suitable micro-organism for use in the present invention include bacteria, moulds and/or yeast.

The micro-organism may be a naturally occurring micro-organism or it may be a transformed micro-organism. The micro-organism may also be a combination of suitable micro-organisms.

It is to be understood that where reference is made in the present specification, including the accompanying claims to 'a' micro-organism or 'an' anti-microbial agent, such reference is meant to include one or more micro-organisms or one or more anti-microbial agents, and mixtures thereof, unless it is specifically stated otherwise in the text.

Preferably the micro-organism is a lacetic acid bacterium (LAB). Preferably the LAB is capable of normal growth and development.

Optionally the LAB may be transformed by different techniques such as genetic techniques.

As used herein the term transformed encompasses recombinant micro-organisms. The term "recombinant micro-organism" means a micro-organism which carries a recombinant nucleotide sequence coding for an exogenous gene. The transformed LAB may also have the capacity for example to utilise different enzyme substrates as a carbon source, to ferment at a different temperature range, exhibit resistance to bacteriophage attack, be capable of quicker capacity to replicate following rehydration in the gut when compared to the parent. Advantageously a recombinant micro-organism may be able to have an increased tolerance to the low pH values experienced in the gut of the consumer on its route to the lower gut.

In a preferred aspect, the micro-organism may be selected from the group consisting of lacetic acid bacterial genera such as *Lactococcus*, *Streptococcus*, *Pediococcus*, *Enterococcus*, *Leuconostoc*, *Carnobacterium*, *Propionibacterium*, *Bifidobacterium* and *Lactobacillus* or combinations thereof.

Preferably, the microorganism according to the present invention may be a bacterium from the genus *Bifidobacterium* and/or *Lactobacillus*.

Preferably, the microorganism according to the present invention may be one or more of the following microorganisms *Bifidobacterium lactis*, *Bifidobacterium longum*, *Bifidobacterium breve*, *Bifidobacterium animalis*.

Suitably, the microorganism according to the present invention is *Bifidobacterium* sp. 420 bacterium.

For the avoidance of doubt, the taxonomic name for *Bifidobacterium* sp. 420 is *Bifidobacterium lactis* 420. These terms are used herein interchangeably.

The complete intestinal tract comprises approximately 1014 bacterial cells. It has been reported that the physiological effects of bacteria are observed at minimum cell count of $10^4$-$10^6$ per gram of intestinal content. Thus, concentration of the probiotic depends on the average of daily dose consumed that is directly dependent on the number of viable probiotic micro-organisms available at end of shelf life.

According to the present invention the water-in-oil preparation may be characterised with viable lacetic acid micro-organisms in the range of from about $10^4$-$10^8$ cfu/g approximately 12 weeks after the day of production.

Preferably the viable lacetic acid micro-organism is added to the continuous oil phase of the hydrophobic combination as described herein in a powder form. The viable lacetic acid micro-organism may be a lyophilised, freeze-dried or spray dried culture of lacetic acid micro-organisms as described above.

Advantageously the addition of the viable lacetic acid micro-organism to the continuous oil phase in powder form facilitates a quicker and more uniform redistribution in the oil phase.

Preparation

Any probiotic preparation (for example a water-in-oil preparation) that can benefit from the probiotic composition or from being prepared by a method according to the present invention may be used in the present invention. These include but are not limited to vegetable probiotic foods, dairy probiotic foods, dairy food-derived products such as spreads, cosmetic and pharmaceutical products. Preferably the probiotic preparations are vegetable water-in-oil foods, dairy probiotic foods, dairy food-derived products such as spreads, cosmetic and pharmaceutical products.

It is within the context of the present invention that the fat content of these products may be in the range of from about 5% to 98% wt.

In a preferred aspect the probiotic preparation is peanut butter.

As stated above, a spread is an edible oil product that is spreadable. It is composed of edible oils and water in the form of an emulsion of the type water-in-oil. Examples of spreads include butter, margarine and low fat spreads.

By way of example the composition as described herein can further be used as an ingredient in food products such as American cheese sauce, anti-caking agent for grated & shredded cheese, chip dip, cream cheese, dry blended whip topping fat free sour cream, freeze/thaw dairy whipping cream, freeze/thaw stable whipped tipping, low fat and light natural cheddar cheese, low fat Swiss style yoghurt, aerated frozen desserts, hard pack ice cream, label friendly, improved economics & indulgence of hard pack ice cream, low fat ice cream: soft serve, barbecue sauce, cheese dip sauce, cottage cheese dressing, dry mix Alfredo sauce, mix cheese sauce, dry mix tomato sauce, peanut butter and others.

The present invention also provides a method of preparing a food or a food ingredient, the method comprising admixing the water-in-oil composition according to the present invention with another food ingredient.

Advantageously, the present invention relates to water-in-oil product that has been contacted with the water-in-oil composition of the present invention (and optionally with other components/ingredients), wherein the water-in-oil composition is used in an amount to be capable of imparting nutrition and/or health benefits of the product.

As used herein the term "contacted" refers to the indirect or direct application of the water-in-oil composition of the present invention to the product. Examples of the application methods which may be used, include, but are not limited to, treating the product in a material comprising the water-in-oil composition, direct application by mixing the water-in-oil composition with the product, spraying the water-in-oil composition onto the product surface or dipping the product into a preparation of the water-in-oil composition.

Where the product of the invention is a foodstuff, the water-in-oil composition of the present invention is preferably admixed with the product.

For some applications, it is important that the water-in-oil composition is made available on or to the surface of a product to be affected/treated. This allows the water-in-oil composition to impart one or more of the following favourable characteristics: nutrition and/or health benefits.

The compositions of the present invention may be applied to intersperse, and/or impregnate a product with a controlled amount of the viable micro-organism.

In a preferred aspect the composition of the present invention is used for the formation of water-in-oil spreads.

In another preferred aspect the composition of the present invention is used for the formation of water-in-oil butter.

Ingredients

The probiotic composition suitable for forming a probioticl preparation as described herein may comprise a number of optional ingredients such as flavouring, flavouring sugars (e.g., lactose) salt, preservatives, acidifiers, vitamins, colouring materials, etc.

Preferably the level of flavouring materials is less than 0.5 wt. %, for example 0.01 to 0.2 wt. %. Preferably the level of salt (sodium chloride) is from 0-4 wt. %, more preferred 0.1 to 3 wt. %, most preferred 0.3 to 1.7 wt %.

Preservatives are preferably incorporated at a level of 0-4 wt. %, more preferred 0.01 to 1 wt. %, most preferred 0.05 to 0.3 wt %. Especially preferred is the use of potassium sorbate. A preferred colouring material is beta carotene; preferred levels of colouring material are from 0-1 wt. %, more preferred 0.01 to 0.2 wt. %. Acidifiers may be incorporated to bring the pH of the product to the desired level, preferably the pH of the product is from 3 to 10, more preferably 3.5 to 7. A suitable acidifier is for example lacetic acid or citric acid.

The probiotic preparation may optimally comprise a thickening agent or combination of thickening agents. The presence of a thickening agent can improve the oral response of the dispersion. A particularly preferred thickening agent is xanthan gum. The structure produced by such thickening agent may break down to some extent but prevents the product from getting very thin rapidly and causes some residual viscosity to be maintained, leading to a desirable consumer property. Other gelling agents which may be included are gelatin, carrageenan, agar, alginate, gellan, pectin, furcelleran and gelling starch mixture of amylose and amylopectin, a gelling maltodextrin and a rapid gelling starch such as those described in U.S. Pat. No. 5,338,560, herein incorporated by reference. The thickening and gelling agents may be present in an amount of up to 10 wt. %, preferably 0.01 to 5 wt. % most preferably 0.01 to 3 wt. %.

To obtain optimal organoleptic characteristics, it is preferred for a water-in-oil preparation to have a continuous phase that melts at a temperature between about 20° C., and about 45° C., more preferably between about 30° C. and about 37° C. This facilitates breakdown in the mouth and prevents the water-in-oil product from being perceived as waxy.

The probiotic composition may comprise other ingredients as is considered desirable in view of the envisaged use by the consumer of the end product. For example, the probiotic composition may comprise colouring matter, e.g. beta-carotene, taste and flavour compounds, e.g., sodium chloride, or non-gelling milk protein, preservative, e.g., potassium sorbate, and thickening agents, e.g., non-gelling starch and/or protein and gums, e.g., xanthan gum.

Combination with Other Components

The probiotic composition of the present invention may be used in combination with other components.

Optionally or in addition the present invention is capable of providing a medical or physiological benefit to the consumer.

Examples of other suitable components which can be added to the composition include one or more of: thickeners, gelling agents, emulsifiers, binders, crystal modifiers, sweeteners (including artificial sweeteners), rheology modifiers, stabilisers, anti-oxidants, dyes, enzymes, carriers, vehicles, excipients, diluents, lubricating agents, flavouring agents, colouring matter, suspending agents, disintegrants, granulation binders, cholesterol reducing agents (such as sterols and stanols) etc. Preferably the other components include yeast extracts and magnesium ions ($Mg^{2+}$). These other components may be prepared by use of chemical and/or enzymatic techniques and/or isolated from their natural environment.

As used herein the term "thickener or gelling agent" as used herein refers to an agent or a substance that prevents separation by slowing or preventing the movement of particles, either droplets of immiscible liquids, air or insoluble solids. Thickening occurs when individual hydrated molecules cause an increase in viscosity, slowing the separation in the cheese product. Gelation occurs when the hydrated molecules link to form a three-dimensional network that traps the particles, thereby immobilizing them in the cheese product.

The term "stabiliser" as used here is defined as an ingredient or combination of ingredients that keeps a product (e.g. a water-in-oil product) from changing over time. The term changing over time may be used in relation to for example colour changes, rehydration of the viable lacetic acid microorganism which may result in prepature spoilage of product or general reduction of the shelf life of the water-in-oil product.

The term "emulsifier" as used herein refers to an ingredient or combination of ingredients (e.g. a water-in-oil product) that prevents the separation of emulsions. Emulsions are two immiscible substances, one present in droplet form, contained within the other. Emulsions can consist of oil-in-water, where the droplet or dispersed phase is oil and the continuous phase is water; or water-in-oil, where the water becomes the dispersed phase and the continuous phase is oil.

Preferably the emulsion as described herein is a water-in-oil emulsion.

Emulsifiers have a polar group with an affinity for water (hydrophilic) and a non-polar group that is attracted to oil (lipophilic). They are absorbed at the interfaces of the two substances, providing an interfacial film acting to stabilise the emulsion. The hydrophilic/lipophilic properties of emulsifiers are affected by the structure of the molecule. These properties are identified by the hydrophilic/lipophilic balance (HLB) value. Low HLB values indicate greater lipophilic tendencies which are used to stabilise water-in-oil emulsions. High HLB values are assigned to hydrophilic emulsifiers, typically used in oil-in-water emulsions. These values are derived from simple systems.

Because different types of water-in-oil products can be prepared according to the method described herein often contain other ingredients that affect the emulsification properties, the HLB values may not always be a reliable guide for emulsifier selection.

The term "crystal modifier" as used herein refers to an ingredient (e.g. a water-in-oil preparation ingredient) that affects the crystallisation of either fat or water. Stabilisation of ice crystals is important for two reasons. The first is directly related to the product stability from a separation standpoint. The more freeze/thaw cycles a water-in-oil product encounters, the larger the ice crystals become. These large crystals can break down product structure, either naturally occurring, as in the case of cell walls, or that which is created by "elation".

Because the water is no longer held in place, the water-in-oil product may exhibit excessive weeping after thawing which may lead to rehydration of the micro-organism. Furthermore, in the case of a product that is consumed frozen, these large crystals may result in an undesirable, gritty mouth feel.

"Carriers" or "vehicles" mean materials suitable for compound administration and include any such material known in the art such as, for example, any liquid, gel, solvent, liquid diluent, solubilizer, or the like, which is non-toxic and which does not interact with any components of the composition in a deleterious manner.

Examples of nutritionally acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Examples of excipients include one or more of: microcrystalline cellulose and other celluloses, lactose, sodium citrate, calcium carbonate, dibasic calcium phosphate, glycine, starch, milk sugar and high molecular weight polyethylene glycols.

Examples of disintegrants include one or more of: starch (preferably corn, potato or tapioca starch), sodium starch glycollate, croscarmellose sodium and certain complex silicates.

Examples of granulation binders include one or more of: polyvinylpyrrolidone, hydroxypropylmethylcellulose (HPMC), hydroxypropylcellulose (HPC), sucrose, maltose, gelatin and acacia.

Examples of lubricating agents include one or more of: magnesium stearate, stearic acid, glyceryl behenate and talc.

The other components may be used simultaneously (e.g. when they are in admixture together or even when they are delivered by different routes) or sequentially (e.g. they may be delivered by different routes).

Preferably, when the composition of the present invention is admixed with any other components, the lacetic acid micro-organism remain viable.

Preferably the lacetic acid micro-organism as described herein becomes rehydrated and thus acquires the capacity to exert its nutritional and/or health benefits upon ingestion by the consumer.

As used herein the term "component suitable for animal or human consumption" means a component which is or can be added to the composition of the present invention as a supplement which may be of nutritional benefit, a fibre substitute or have a generally beneficial effect to the consumer. Preferably, the ingredients will be able to improve the shelf life of the product and stability of the viable culture.

The components may be prebiotics such as alginate, xanthan, pectin, locust bean gum (LBG), inulin, guar gum, galacto-oligosaccharide (GOS), fructo-oligosaccharide (FOS), lactosucrose, soybean oligosaccharides, palatinose, isomalto-oligosaccharides, gluco-oligosaccharides and xylo-oligosaccharides.

Preferably the prebiotic is added to the probiotic preparation as a polydextrose selected from the group consisting of Litesse™, pectin and maltodextrin.

As used herein the term "binder" refers to an ingredient or a combination of ingredients (e.g. a water-in-oil product ingredient) that binds a product through a physical or chemical reaction. By way of example during "elation" water is absorbed, providing a binding effect. However, binders can also absorb liquids, such as oils, holding them within the water-in-oil preparation. For some embodiments of the present invention binders would be used in low-water preparations.

The optimum amount of the combination which comprises the viable lacetic acid micro-organism in the continuous oil phase to be used according to the present invention will depend on the product and/or the method of contacting the product with the composition and/or the intended use for the same. The amount of viable microorganism used in the compositions should be a sufficient amount to be effective and to remain sufficiently effective in improving the nutrition and/or health benefits of the water-in-oil products containing said composition. This length of time for effectiveness should extend up to at least the time of utilisation of the product.

Preferably the water-in-oil product according to the present invention comprises from about $10^4$-$10^8$ cfu/g of product about 12 weeks after the day of production.

Preparation of the Composition

The probiotic composition (for example a water-in-oil composition) of the present invention may be prepared by an in situ process—of the type mentioned herein. In this case, suitable micro-organisms are present in a hydrophobic medium that is capable of maintaining their viability.

It is preferred that the components of the composition may be prepared in isolation and then be combined together to form the composition.

By way of example the water-in-oil emulsion may be prepared in situ by mixing the water and the oil components in order to form an emulsion. As stated above the emulsification may be obtained by using equipment such as a tubular Scraped Surface Heat Exchanger (SSHE) e.g. Votator™ or a Diacooler™. The in situ produced water-in-oil emulsion may be stored in a form such that when adding to it the combination which comprises probiotic micro-organisms in a hydrophobic medium the cell density of the product would contain approximately from about $10^8$-$10^9$ cfu/g.

According to one of the aspects of the present invention, a hydrophobic combination containing the viable lacetic acid micro-organism in a continuous oil phase is produced in situ (see in situ preparation of the hydrophobic combination above).

Alternatively, the hydrophobic combination of the present invention may be formed for example by combining recombinant lacetic acid micro-organisms in a continuous oil phase.

As stated above, a recombinant micro-organism may carry a recombinant nucleotide sequence. As used herein the term "recombinant nucleotide" means that the nucleotide sequence is derived from a different organism i.e. it is not a self nucleotide sequence.

According to another aspect of the present invention there is provided a method which comprises forming a water-in-oil preparation by providing the above described water-in-oil emulsion which is admixed with a hydrophobic combination comprising a viable lacetic acid micro-organism in a continuous oil phase. It would be appreciated by those of skill in the art that the amount of the hydrophobic combination comprising the viable acid micro-organism in a continuous oil phase would be determined by different factors such as for example the cell density of the hydrophobic combination and the desired end product. It is intended that the end product would contain in the range of approximately from about $10^8$-$10^9$ cfu/g of lacetic acid micro-organism.

The amount of the hydrophobic combination added to the water-in-oil emulsion may be from about 12% to about 0.01% of the total product. Preferably the amount of the hydrophobic combination added to the water-in-oil emulsion may be from about 11% to about 0.05%. Preferably the amount of the hydrophobic combination added to the water-in-oil emulsion may be from about 10% to about 0.1%. Preferably the amount of the hydrophobic combination added to the water-in-oil emulsion may be from about 9% to about 0.5%. Preferably the amount of the hydrophobic combination added to the water-in-oil emulsion may be from about 8% to about 1%. Preferably the amount of the hydrophobic combination added to the water-in-oil emulsion may be from about 7.5% to about 1.5%. Preferably the amount of the hydrophobic combination to the water-in-oil emulsion may be from about 5% to about 2%.

As stated above, by varying the amount of the hydrophobic combination added to the water-in-oil emulsion a product can be obtained which comprises approximately from about $10^4$-$10^8$ cfu/g of viable lacetic acid micro-organisms approximately 12 weeks after the day of production.

Preferably when mixing the water-in-oil emulsion with the hydrophobic combination, the mixture is not subjected to a strenuous physical manipulations or intensive shear treatment. By way of example the mixing of the water-in-oil emulsion and the hydrophobic combination is done in a pinworker or similar type of equipment which would be known to those of skill in the art in order to generate a stable water-in-oil preparation.

Optionally the formed water-in-oil preparation may be packaged.

By producing the composition as described herein in a fat that is suitable for consumption, a water-in-oil product containing said composition would not require labelling as containing an additive.

The composition or optionally each isolated component can advantageously be added into a suitable for forming a water-in-oil preparation for the production of for example a water-in-oil spread or a water-in-oil butter and other water-in-oil based or related products thereof.

Using the composition according to the present invention would advantageously lead to the production of a water-in-oil product which may be capable of imparting a probiotic and/or prebiotic and/or a symbiotic effect on the consumer.

Handling and Packaging

Care should be taken during the handling and packaging of the probiotic preparations, especially water-in-oil preparations such as low-fat water-in-oil spreads and low-fat water-in-oil butters described herein. It has been found that reducing or eliminating pressure may be important in avoiding irreversible damage to the product's stability and thus viability of the lacetic acid micro-organisms.

Minimising or eliminating line pressure after mixing the water-in-oil emulsion with the hydrophobic combination as described herein is highly desirable, although some allowance must be made for the type of packaging equipment being used. In the case of products to be packed in tubs, pressure can be readily minimised, as will be apparent to the person skilled in the art in light of the present disclosure.

Where the water-in-oil product is to be printed on however, consideration must be given to minimum operating pressures required for commercial printing apparatus.

Food

The composition of the present invention or the composition produced by a method according to the present invention may be used as—or in the preparation of—a water-in-oil food. Here, the term "food" is used in a broad sense—and covers food for humans as well as food for animals (i.e. a feed). Preferably the food is for human consumption.

The food may be in the form of a solution or as a solid—depending on the use and/or the mode of application and/or the mode of administration.

When used as—or in the preparation of—a food—such as functional food—the composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

Preferably, the water-in-oil composition is used in the preparation of water-in-oil products containing all components of the composition—i.e. said water-in-oil emulsion and the hydrophobic combination comprising viable lacetic acid micro-organism in continuous oil phase according to the present invention—can be added as an ingredient to for example yoghurt or salad dressings or dips in suitable concentrations—such as for example in concentrations in the final product which offer a daily dose of $10^6$-$10^{10}$ cfu. Preferably the fat content of the water-in-oil product comprises from about 5% to about 98% fat content.

Preferably the water-in-oil product formed using the composition according to the present invention is a water-in-oil spread or a water-in-oil butter or a water-in-oil product derived therefrom.

Food Ingredient

The probiotic composition of the present invention or the composition produced by a method according to the present invention may be used as a food ingredient and/or feed ingredient.

As used herein the term "food ingredient" or "feed ingredient" includes a formulation which is or can be added to functional foods or foodstuffs as a nutritional supplement.

The food ingredient may be in the form of a solution or as a solid—depending on the use and/or the mode of application and/or the mode of administration.

Food Supplements

The probiotic composition of the present invention or produced by a method according to the present invention may be—or may be added to—food supplements.

Functional Foods

The probiotic composition of the present invention or the composition produced by a method according to the present invention, may also be—or may be added to—any functional food.

As used herein, the term "functional food" means a product which is capable of providing not only a nutritional and or health effect but is also capable of delivering a further beneficial effect to the consumer.

Accordingly, functional foods are ordinary foods that have components or ingredients (such as those described herein) incorporated into them that impart to the food a specific functional—e.g. medical or physiological benefit—other than a purely nutritional effect.

Although there is no legal definition of a functional food most of the parties with an interest in this area agree that they are foods marketed as having specific health effects.

Some functional foods are nutraceuticals. Here, the term "nutraceutical" means a food which is capable of providing not only a nutritional effect and/or a taste satisfaction, but is also capable of delivering a therapeutic (or other beneficial) effect to the consumer. Nutraceuticals cross the traditional dividing lines between foods and medicine.

Surveys have suggested that consumers place the most emphasis on functional food claims relating to heart disease. Preventing cancer is another aspect of nutrition which interests consumers a great deal, but interestingly this is the area that consumers feel they can exert least control over. In fact, according to the World Health Organization, at least 35% of cancer cases are diet-related. Furthermore claims relating to osteoporosis, gut health and obesity effects are also key factors that are likely to incite functional food purchase and drive market development.

Fibre Supplement

In another aspect, the probiotic composition of the present invention or the composition produced by a method according to the present invention, may be used as—or in the preparation of—a fibre supplement.

Initially, the success of a food product virtually hinged on the word "fibre" or, subsequently, "bran". Despite conflicting studies on fibre's specific health attributes, the overall consensus among experts and consumers is that most people need more fibre in their diet. Fibre has further proven to be useful for its functional properties, such as water absorption and bulk-building in reduced-fat foods.

Fibre has gone by a number of names over the years, including "roughage," "bulk," "bran", "fibre", "plant residue", "plantix" and "unavailable carbohydrates". Even today, devising a concise, yet complete, definition for dietary fibre is no simple task because dietary fibre is a complex matrix of various components defined differently among various scientific disciplines.

Here, the term fibre is used in the context of food and as such it is referred to as non-digestible material. Specifically, fibre consists of cellulose, hemicellulose, pectins, gums, mucilages and lignin.

Not every fibre source comprises all of these components. Actually, it is the sheer number of potential combinations that results in the wide variety of different physiological and functional effects observed in different fibre ingredients. By the same token, not every fibre source is 100% dietary fibre.

"Total dietary fibre (TDF) is defined as non-digestible carbohydrates," says Diane Lardiere, national sales and marketing manager, Canadian Harvest, Cambridge, Minn. "Wheat bran is only 40% TDF, but is considered a fiber ingredient".

Thus, the probiotic composition of the present invention or produced by a method according to the present invention may be added to—fiber supplements.

It is within the scope of the present invention that the probiotic composition is used as a supplement to a diet in combination with different conventional fiber sources as detailed above.

The recommended dose of fiber intake for adults is between 20 and 35 grams per day or 10-13 grams per every 1000 calories consumed and for children, generally, the intake is based on their age or weight 0.5 grams of fiber per kilogram of body weight (or 0.23 grams per pound of body weight) with an upper limit of 35 grams of fiber per day.

It is also within the scope of the invention to provide a means ensuring that the recommended daily fiber intake (20-35 grams per day or 10-13 grams per every 1000 calories consumed) is achievable. Such tablets, pills, capsules, ovules, solutions or suspensions, can be formulated to substitute for meals and snacks, especially during the beginning of a weight-loss program.

Importantly from a health point of view, when fiber tablets, pills, capsules, ovules, solutions or suspensions are taken with meals, it helps reduce the consequent rise in blood glucose after eating and enhances satiety.

It is also within the scope of this application that the probiotic composition of the present invention be incorporated in a fiber beverage. Research has indicated that soluble fiber, may help support digestive health and that a diet high in soluble fiber (at least 25 grams per day) may help maintain normal cholesterol levels.

Probiotic

According to one aspect of the present invention the water-in-oil composition is used to prepare a water-in-oil product which is capable of modulating the microbial balance of the gastrointestinal tract after consumption of the product. In other words the water-in-oil composition according to the present invention can be used for the production of cheese products which are characterised with probiotic effect.

For some applications, it is believed that the viable lacetic acid micro-organisms in the water-in-oil composition of the present invention can exert a probiotic culture effect in the gastrointestinal tract It is also within the scope of the present invention to add to the water-in-oil composition of the present invention further probiotic cultures.

The term "probiotic culture" as used herein defines a viable micro-organisms which is capable of beneficially affecting the host organism by improving its intestinal microbial balance. The term "probiotic" as used herein also encompasses viable micro-organisms that can stimulate the beneficial branches of the immune system and at the same time decrease most of the inflammatory reactions in the gut. In this regard, the use of the composition of the present invention, containing said probiotic ingredient for anti-cancer therapy and prevention of allergies and ulcerative colitis is also contemplated.

Whilst there are no lower or upper limits for probiotic intake, it has been suggested that at least 10,000 viable cells per ml of product will give the micro-organism a competitive chance within the gut micro-flora.

Whilst there are no lower or upper limits for probiotic intake, it has been suggested that in the range of least $10^4$-$10^{10}$, preferably $10^8$-$10^9$, cfu as a daily does will give the micro-organism a competitive chance within the gut microflora. It is noted that a physiological effect is observed at the lower range of $10^4$, however, it would be apparent to the skilled person that this is dependent on the intake levels of the product consumed.

In addition to the probiotic effect that the microorganism according to the present invention may have, it is also within the scope of the present invention to provide prebiotics as other compounds that can be included with the composition.

Prebiotics

As stated above the composition which is suitable for forming a probiotic preparation may have a prebiotic effect on the consumer. Here, a prebiotic is:

"a non-digestible food ingredient that beneficially affects the host by selectively stimulating the growth and/or the activity of one or a limited number of bacteria in the colon." (*Am Clin Nutrit*, 2001; 73:406 S-409S.).

According to one consensus report (van Loo et al., 1999, *Br. J. Nutr.*, 81: 121-132) the definition for prebiotic is an increase in the number and/or activity of mainly bifidobacteria or lacetic acid bacteria in the gastrointestinal tract. Here, it is known that: bifidobacteria may help fight a wide range of harmful and food-poisoning bacteria, including the potentially fatal *E. coli* 0157 and *E. coli* H88. In addition it is known that bifidobacteria can prevent young children suffering from diarrhoea. *Lactobacillus* GG can be helpful in treating antibiotic-associated diarrhoea while and has also been shown effective at treating some cases of travellers' diarrhoea and rotavirus infection, the most common cause of diarrhoea in children world-wide.

The prebiotic component of the composition of the present invention is characterised with slow fermentation in the large bowel. Such prebiotics can exert a positive effect on the gut micro-flora, specifically in the left side of the colon, an area of the gut that is especially prone to disorders in particular bowel cancer and ulcerative colitis.

Prebiotics are typically non-digestible carbohydrate (oligo- or polysaccharides) or a sugar alcohol which is not degraded or absorbed in the upper digestive tract. Known prebiotics used in commercial products and useful in accordance with the present invention include inulin (fructo-oligosaccharide, or FOS) and transgalacto-oligosaccharides (GOS or TOS).

Other suitable, prebiotics include palatinoseoligosaccharide, soybean oligosaccharide, gentiooligosaccharide, xylooligomers, non-degradable starch, lactosaccharose, lactulose, lactitol, maltitol, pectin, maltodextrin, polydextrose (i.e. Litesse®) or the like.

The prebiotic may be administered simultaneously with (e.g. in admixture together with or delivered simultaneously by the same or different routes) or sequentially to (e.g. by the same or different routes) the water-in-oil product according to the present invention.

For example, the present invention contemplates the use of a water-in-oil preparation comprising a water-in-oil emulsion and a hydrophobic combination, said hydrophobic combination comprising a viable lacetic acid micro-organism in a continuous oil phase with a prebiotic wherein the prebiotic has a nutritional and/or health benefit on the consumer.

Symbiotic

The present invention also contemplates using both pre- and probiotics as ingredients in a combination along with the composition of the present invention which when combined, become symbiotics.

The purpose of this is to combine the effects of new beneficial bacteria and the stimulation of the body-own beneficial bacteria. There is a high potential in the development and the consumption of such mixtures, since some of these may well show powerful synergistic nutritional and/or health effects.

Thus the composition of the present invention may be specifically designed to form a water-in-oil product containing different components which can provide a symbiotic effect to the consumer.

Pharmaceutical

The composition of the present invention or the composition produced by a method of the present invention may be used as—or in the preparation of—a pharmaceutical. Here, the term "pharmaceutical" is used in a broad sense—and covers pharmaceuticals for humans as well as pharmaceuticals for animals (i.e. veterinary applications). In a preferred aspect, the pharmaceutical is for human use and/or for animal husbandry.

The pharmaceutical can be for therapeutic purposes—which may be curative or palliative or preventative in nature. The pharmaceutical may even be for diagnostic purposes.

When used as—or in the preparation of—a pharmaceutical, the composition of the present invention may be used in conjunction with one or more of: a pharmaceutically acceptable carrier, a pharmaceutically acceptable diluent, a pharmaceutically acceptable excipient, a pharmaceutically acceptable adjuvant, a pharmaceutically active ingredient.

The pharmaceutical may be in the form of a solution or as a solid—depending on the use and/or the mode of application and/or the mode of administration.

Preferably the effect of the viable lacetic acid micro-organism is exerted following rehydration of the micro-organism for example upon ingestion of the pharmaceutical comprising the composition as described herein.

In one aspect, the composition according to the present invention may be administered in an aerosol, for example by way of a nasal spray, for instance for administration to the respiratory tract.

In another aspect the composition according to the present invention may be advantageously be administered in an encapsulated form having a hard exterior or soft exterior and a liquid or fluid interior or in a chewable capsule. By way of example the hydrophobic combination may be incorporated in a fish oil capsule for ingestion.

Pharmaceutical Ingredient

The composition, of the present invention or the composition produced by a method of the present invention, may be used as pharmaceutical ingredients. Here, the composition may be the sole active component or it may be at least one of a number (i.e. 2 or more) active components.

The pharmaceutical ingredient may be in the form of a solution or as a solid—depending on the use and/or the mode of application and/or the mode of administration.

Forms

The composition of the present invention (including a composition when produced by the method of the present invention) may be used in any suitable form—whether when alone or when present in combination with other components or ingredients. Likewise, combinations comprising the composition of the present invention and other components and/or ingredients (i.e. ingredients—such as food ingredients, pharmaceutical ingredient or functional food ingredients) may be used in any suitable form.

The composition of the present invention may be used in the form of solid or liquid preparations or alternatives thereof. Examples of solid preparations include, but are not limited to tablets, capsules, dusts, granules and powders which may be wettable, spray-dried, freeze-dried or lyophilised. Examples of liquid preparations include, but are not limited to, aqueous, organic or aqueous-organic solutions, suspensions and emulsions. Preferably the liquid preparation as described herein is a water-in-oil preparation comprising a water-in-oil emulsion having a fat content of approximately from about 5% to about 98%.

Suitable examples of preparations include one or more of: tablets, pills, capsules, ovules, solutions or suspensions, which may contain flavouring or colouring agents, for immediate-, delayed-, modified-, sustained-, pulsed- or controlled-release applications. In regard to a controlled-release application it would be possible to regulate for example the addition of the hydrophobic combination comprising the viable lacetic acid micro-organism in a continuous oil phase thereby allowing a greater control of the number of cells in the end probiotic product.

By way of example, if the composition of the present invention is used in a tablet form—such for use as a functional ingredient—the tablets may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparations include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Preferred excipients for the preparations include lactose, sucrose, maltose, starch, a cellulose, milk sugar or high molecular weight polyethylene glycols.

The forms may also include gelatin capsules; fiber capsules, fiber tablets etc.; or even fiber beverages.

EXAMPLES

The present invention will now be described by way of examples, and with reference to the accompanying figures:

FIGURES

FIG. 1. Incorporation of freeze-dried *Bifidobacteria* in liquid oil suspension into water-in-oil emulsions.

Figure 2:
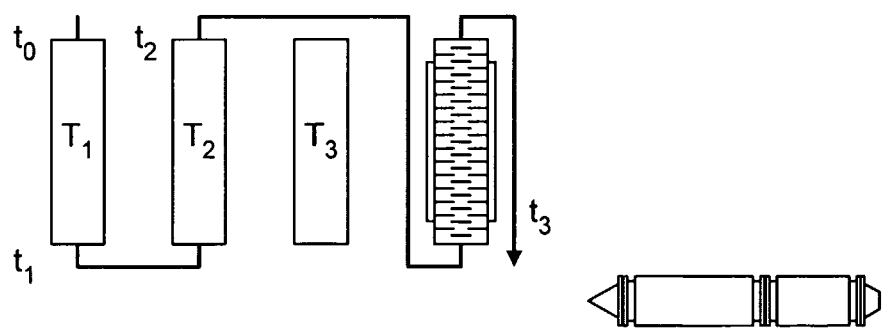

FIG. 2. A representation of a SSHE apparatus and a pin worker suitable for forming a water-in-oil product.

EXAMPLE 1

Method of Preparing a Hydrophobic Component

Described is an example that can be used for the formation of a water-in-oil product comprising a viable lacetic acid micro-organism. FIG. 1 shows the formation of the water-in-oil emulsion that is prepared before it is mixed with the viable lacetic acid *Bifidobacterium* resuspended and/or redistributed in a continuous oil phase.

The water-in-oil emulsion can be formed using an SSHE apparatus which is well known to those of skill in the art.

The hydrophobic component (probiotic suspension) may be made as follows: —1 liter is sufficient for 200 kgs of spread, unless a further dilution is desired.

You have 200 g samples therefore 0.04 g is within each 200 gs. This equals 0.02% of "active" or "viable" material.

4% Probiotic *Bifido* species 420
94% Liquid oil (partially hydrogenated or fully unsaturated)
2% Grindsted PS 209 (of which 10% is monoester)
1 liter of material
40 g Probiotic *Bifidobacterium* sp. 420
940 g Liquid Oil
20 g Grindsted PS 209 (comprises triglyceride and a monoester)

Procedure.

1. Heat liquid oil and PS 209 to 80° C. (or make dilution of 1 part PS 209+5 parts liquid oil, heat to 80° C. and add to balance of liquid oil)
2. Cool solution to 20° C. Gel will form.
3. Break gel by agitation/mixing action and add Probiotic *Bifidobacterium* species 420, and disperse into oil. Stop mix action once dispersed. Probiotic will stay in suspension.
4. Store at 5° C. until required for use.

At this stage the probiotic suspension can be packaged and stored for later use.

It should be noted that dosage/ratio of probiotics used to form suspension is dependant upon the required log value, product size, and ability to precisely match infeed capacity of a given emulsion with the correct ratio of probiotic suspension. As an example see Table 1 below.

TABLE 1

Titration of dosage/ratio of probiotics.

| Emulsion Product size in grams | % of bacterium required | Bifido bacterium required in final product (grams) | concentration of probiotic to make 1 litre of probiotic solution (grams) |
|---|---|---|---|
| 100 | 0.02 | 0.02 | 20 |
| 150 | 0.02 | 0.03 | 30 |

TABLE 1-continued

Titration of dosage/ratio of probiotics.

| Emulsion Product size in grams | % of bacterium required | Bifido bacterium required in final product (grams) | concentration of probiotic to make 1 litre of probiotic solution (grams) |
|---|---|---|---|
| 200 | 0.02 | 0.04 | 40 |
| 250 | 0.02 | 0.05 | 50 |
| 400 | 0.02 | 0.08 | 60 |
| 450 | 0.02 | 0.09 | 90 |
| 500 | 0.02 | 0.1 | 100 |

If we wish to increase log then we simply multiply by 10. We also adjust dilution, concentration, viscosity by adjusting ratio of bacterium to the blend of triglyceride suspension, and also adjusting level of its saturation and unsaturation, and further, by adjusting inclusion of monoester.

EXAMPLE 2

Method of Preparing a Water-in-Oil Preparation

We provide experimental data showing the production of a water-in-oil product using the composition according to the present invention. Here is also shown a schematic representation of an SSHE apparatus that can be used in accordance with the present invention (see FIG. 2). The SSHE apparatus comprises units $T_1$ and $T_2$. Unit $T_3$ represents a pin worker that is suitable for mixing the water-in-oil emulsion prepared in units $T_1$ and $T_2$ and the hydrophobic combination which comprises the viable lacetic acid *Bifidobacterium* sp. 420 in a continuous oil phase.

The composition used in this experiment contains the following components (see Table 2 below).

TABLE 2

Components of the water-in-oil product:

| Ingredients: | % | Kg batch, kg |
|---|---|---|
| Water | 55.465 | 27.733 |
| Salt | 1.0 | 0.5 |
| Litesse | 1.8 | 0.9 |
| LFS 560 | 0.7 | 0.35 |
| Butter milk powder | 2.0 | 1.0 |
| Probiotic in a continuous oil phase | 0.04 | 0.02 |
| Potassium sorbate | 0.1 | 0.05 |
| EDTA | 0.015 | 0.0075 |
| Rape seed oil | 22.79 | 11.4 |
| Soya | 15.2 | 7.6 |
| Dimodan U/J | 0.8 | 0.4 |
| PGPR 90 | 0.1 | 0.05 |
| Beta carotene | 4 ppm | 0.0016 |
| Flavor 2599 | 0.01 | 0.005 |
| PH 5.5 adjusted with citric acid | | |
| Total | 100 | 50 |

All components listed in Table 2, apart from the probiotic lacetic acid bacteria in the continuous oil phase, were added to unit $T_1$. This is the first unit of the SSHE apparatus. The temperature of the ingredients entering unit $T_1$ is identified as $t_0$ see Table 3.

The temperature of the water-in-oil emulsion leaving unit $T_1$ of the SSHE and entering unit $T_2$ of the SSHE is termed $t_1$ see Table 3. The temperature of the water-in-oil emulsion leaving unit $T_2$ of the SSHE and entering mixing unit $T_3$ is termed $t_2$ see Table 3 below.

TABLE 3

Parameters used in preparing the water-in-oil product.

| | Capacity | Cooling temp. ° C. | | | Product temperature ° C. | | | | | |
|---|---|---|---|---|---|---|---|---|---|---|
| Sample | Kg/h | $T_1$ | $T_2$ | $T_3$ | $t_0$ | $t_1$ | $t_2$ | $t_3$ | $t_4$ | $t_5$ | $t_6$ |
| 1.1 | 39.4/0.8 | −4.8 | −8.3 | | 37.5 | 7.3 | 4.7 | 11.9 | | | |
| 1.2 | 48.2/1 | −10.0 | −7.6 | | 39.4 | 10.9 | 5.0 | 10.2 | | | |
| 1.3 | 48.1/1 | −9.4 | −6.9 | | 39.1 | 5.0 | 6.2 | 11.2 | | | |
| 1.4 | 48.3/1 | −9.7 | −6.7 | | 38.5 | 4.6 | 6.1 | 11.4 | | | |

| RPM | | | | | Pressure | |
|---|---|---|---|---|---|---|
| $T_1$ | $T_2$ | $T_3$ | PM | M | Bar | Remarks |
| 400 | 400 | | | 100 | 6.2 | A bit streaks |
| 400 | 400 | | | 100 | 5.8 | Good |
| 600 | 600 | | | 50 | 7.1 | Good |
| 600 | 600 | | | 100 | 7.2 | Good |

It should be noted that in sample 1.1 there was too much streaking at 50 RPM (revolutions per minute) and the RPM had to be increased to 100 RMP.

The mixing unit $T_3$ is used to mix and/or resuspend the water-in-oil emulsion with the hydrophobic combination comprising the viable lacetic acid micro-organism in a continuous oil phase. The mixing unit $T_3$ does not have any strenuous physical manipulations. The lack of strenuous physical manipulations within $T_3$ allow the lacetic acid bacteria to remain viable in the water-in-oil suspension. Also the capacity of the viable cells which are redistributed in a continuous oil phase to localize to the fat globules within the water-in-oil product may influence their viability.

The evaluation of the samples at 5° C. showed the following characteristics:

sample 1.1 was soft, aerated and a bit streaked,
sample 1.2 was former and more streaked,
sample 1.3 very streaked and soft,
sample 1.4 good consistency and only a bit streaked.

The viable lacetic acid bacterium used in these experiments is *Bifidobacterium* sp. 420. However it is envisaged that other probiotic lacetic acid bacteria which have been prepared by freeze-drying or spray drying may be incorporated in s similar manner.

EXAMPLE 3

Preparation of a Water-in-Oil Product

Here we provide experimental data showing the production of a water-in-oil product using the composition containing no prebiotic component in the water-in-oil emulsion. The same SSHE apparatus set up is used as that shown in FIG. 2. The SSHE apparatus comprises units $T_1$ and $T_2$. Unit $T_3$ represents a pin worker that is suitable for mixing the water-in-oil emulsion prepared in units $T_1$ and $T_2$ and the hydrophobic combination which comprises the viable lacetic acid *Bifidobacterium* sp. 420 in a continuous oil phase.

The composition used in this experiment for forming the emulsion contains the following components (see Table 4 below).

TABLE 4

Components of the water-in-oil product:
Composition of the product:

| Ingredients: | % | Kg batch, kg |
|---|---|---|
| Rape seed oil | 22.19 | 11.1 |
| Soya 35 | 14.8 | 7.4 |
| Dimodan U/J | 0.7 | 0.35 |
| PGPR 90 | 0.3 | 0.15 |
| Beta carotene | 0.004 | 0.002 |
| Skim-milk powder | 0.25 | 0.125 |
| LFS 560 | 3.0 | 1.5 |
| Salt | 1.5 | 0.75 |
| Potassium sorbate | 0.2 | 0.1 |
| Citric acid | 0.05 | 0.025 |
| Water | 56.996 | 28.498 |
| Flavor 2599 | 0.01 | 0.005 |
| pH 5.5 adjusted with citric acid | | |
| Total | 100 | 50 |

All components of listed in Table 4 were added to unit $T_1$. This is the first unit of the SSHE apparatus. The temperature of the ingredients entering unit $T_1$ is identified as to see Table 5. Please note that the components listed in Table 4 above do not incorporate the prebiotic component Litesse™.

The temperature of the water-in-oil emulsion leaving unit $T_1$ of the SSHE and entering unit $T_2$ of the SSHE is termed $t_1$ see Table 5. The temperature of the water-in-oil emulsion leaving unit $T_2$ of the SSHE and entering mixing unit $T_3$ is termed $t_2$ see Table 5 below.

TABLE 5

Parameters used in preparing the water-in-oil product.

| Sample | Capacity Kg/h | Cooling temp. ° C. | | | Product temperature ° C. | | | | | | |
|---|---|---|---|---|---|---|---|---|---|---|---|
| | | $T_1$ | $T_2$ | $T_3$ | $t_0$ | $t_1$ | $t_2$ | $t_3$ | $t_4$ | $t_5$ | $t_6$ |
| 2.1 | 39.7/0.8 | −9.9 | −4.7 | | 39.8 | 13.3 | 8.9 | 14.5 | | | |
| 2.2 | 39.7/0.8 | −9.9 | −4.8 | | 39.9 | 19.1 | 9.0 | 14.6 | | | |
| 2.3 | 39.7/1.0 | −9.8 | −5.2 | | 39.0 | 11.3 | 8.9 | 16.2 | | | |
| 2.4 | 39.7/1.0 | −9.8 | −5.1 | | 38.5 | 12.2 | 8.9 | 18.3 | | | |

| RPM | | | | | Pressure | |
|---|---|---|---|---|---|---|
| $T_1$ | $T_2$ | $T_3$ | PM | M | Bar | Remarks |
| 600 | 600 | | | 50 | 5.4 | |
| 600 | 600 | | | 100 | 4.8 | |
| 600 | 600 | | | 200 | 6.3 | |
| 600 | 600 | | | 500 | 5.9 | |

The revolutions per minute (RPM) used in the present experiment were higher, going up to approximately 500 RPM) compared to RPM used for the experiment shown in Example 2 which do not exceed 100 RPM.

The mixing unit $T_3$ is used to mix and/or resuspend the water-in-oil emulsion with the hydrophobic combination comprising the viable lacetic acid micro-organism in a continuous oil phase. The mixing unit $T_3$ does not carry out any strenuous physical manipulations. The lack of strenuous physical manipulations within $T_3$ allow the lacetic acid bacteria to remain viable in the water-in-oil suspension. Also the capacity of the viable cells which are redistributed in a continuous oil phase to localize to the fat globules within the water-in-oil product may influence their viability.

The viable lacetic acid bacterium used in this experiment is also *Bifidobacterium* sp. 420 in the amount of 0.04 wt %. However it is envisaged that other probiotic lacetic acid bacteria which have been prepared by freeze-drying or spray drying may be incorporated in a similar manner.

EXAMPLE 4

Viability of Probiotic Micro-Organisms in Water-in-Oil Products

The composition suitable for forming a water-in-oil product containing viable lacetic acid bacteria was tested in order to determine the period of time within which the lacetic acid bacteria remain viable in the product.

It has been reported that some water-in-oil products which comprise viable, lacetic acid bacteria the viability of the bacteria dramatically drops by as much as 50% soon after the day of manufacture.

Using the composition according to the present invention it was possible to obtain a stable water-in-oil product comprising viable lacetic acid bacteria which remain viable for prolonged periods of time.

Analysis is provided of *Bifidobacteria* sp. 420 in probiotic water-in-oil spread fresh and for up to 10 weeks for sample 1.1 to 1.4 obtained from the method of example 2 and for up to two weeks for sample 2.1 to 2.4 obtained from example 3 (see Table 6 below).

After DOM (Date of Manufacturing)+2 weeks a slight decrease in cell count is observed.

TABLE 6

Number of samples tested. Cell counts [cfu/g]

| Sample | Total | Broken | |
|---|---|---|---|
| 1.1 | 12 | 3 | |
| 1.2 | 12 | 3 | |
| 1.3 | 13 | 2 | |
| 1.4 | 4 | 2 | divided up in smaller parts - stored anaerobic |
| 2.1 | 16 | 1 | |
| 2.2 | 13 | 2 | |
| 2.3 | 15 | 1 | |
| 2.4 | 3 | 1 | divided up in smaller parts - stored anaerobic |

TABLE 7

Viability of lactic acid bacteria in the water-in-oil end product. Cell counts [cfu/g]

Bifidobacteria

| Sample | Fresh DOM + 1 week | DOM + 2 weeks 11.03.04 | DOM + 3 weeks 18.03.04 | DOM + 4 weeks 25.03.04 | DOM + 5 weeks 01.04.04 |
|---|---|---|---|---|---|
| 1.1 | $1.2 \times 10^8$ | $6.5 \times 10^7$ | $5.1 \times 10^7$ | $1.1 \times 10^8$ | $8.8 \times 10^6$ |
| 1.2 | $7.4 \times 10^7$ | $7.9 \times 10^7$ | $2.3 \times 10^7$ | $1.3 \times 10^8$ | $6.3 \times 10^7$ |
| 1.3 | $7.1 \times 10^7$ | $4.3 \times 10^7$ | $1.5 \times 10^7$ | $8.6 \times 10^7$ | $2.5 \times 10^7$ |
| 1.4 | $8.6 \times 10^7$ | $3.7 \times 10^7$ | $1.5 \times 10^7$ | $3.6 \times 10^7$ | $1.7 \times 10^7$ |
| 2.1 | $2.4 \times 10^7$ | $4.0 \times 10^6$ | | | |
| 2.2 | $2.9 \times 10^7$ | $4.2 \times 10^6$ | | | |
| 2.3 | $4.9 \times 10^7$ | $4.7 \times 10^6$ | | | |
| 2.4 | $5.3 \times 10^7$ | $6.6 \times 10^6$ | | | |

Bifidobacteria

| Sample | DOM + 6 weeks 08.04.04 | DOM + 7 weeks 15.04.04 | DOM + 8 weeks 22.04.04 | DOM + 9 weeks 29.04.04 | DOM + 10 weeks 06.05.04 |
|---|---|---|---|---|---|
| 1.1 | $2.0 \times 10^5$ | $1.4 \times 10^6$ | $3.1 \times 10^4$ | $1.6 \times 10^5$ | $3.0 \times 10^3$ |
| 1.2 | $4.0 \times 10^6$ | $6.1 \times 10^5$ | $1.7 \times 10^4$ | $1.1 \times 10^6$ | $1.1 \times 10^6$ |
| 1.3 | $4.3 \times 10^6$ | $1.0 \times 10^6$ | $6.2 \times 10^4$ | $7.4 \times 10^4$ | $1.3 \times 10^5$ |
| 1.4 | $8.3 \times 10^5$ | $3.4 \times 10^5$ | $2.7 \times 10^4$ | $1.4 \times 10^5$ | $1.4 \times 10^4$ |

EXAMPLE 5

Further Viability Trials for the Probiotic Micro-Organisms in Water-in-Oil Products Another series of tests were conducted which used the methodology of Example 2.

Samples 1 to 4 were obtained using the same composition and methodology of samples 1.1 to 1.4 of Example 4.

Using the composition prepared by a method according to the present invention it was possible to obtain a stable water-in-oil product comprising viable lacetic acid bacteria which remain viable for prolonged periods of time, specifically the water-in-oil product contains the $10^5$ to $10^6$ CFU/g after 13 weeks.

TABLE 8

Viability of Bifidobacteria (cfu/g) in the water-in-oil product

| Sample | DOM + 1 week | DOM + 2 week | DOM + 3 week | DOM + 4 week | DOM + 5 week |
|---|---|---|---|---|---|
| 1 | $1.3 \times 10^8$ | $7.2 \times 10^7$ | $3.8 \times 10^7$ | $3.0 \times 10^7$ | $2.6 \times 10^7$ |
| 2 | $1.1 \times 10^8$ | $5.3 \times 10^7$ | $5.2 \times 10^7$ | $3.4 \times 10^7$ | $3.1 \times 10^7$ |
| 3 | Failed | $4.7 \times 10^7$ | $9.6 \times 10^7$ | $7.6 \times 10^7$ | $4.5 \times 10^7$ |
| 4 | Failed | $8.5 \times 10^7$ | $5.4 \times 10^7$ | $3.0 \times 10^7$ | $2.8 \times 10^7$ |

| Sample | DOM + 6 week | DOM + 7 week | DOM + 9 week | DOM + 11 week | DOM + 13 week |
|---|---|---|---|---|---|
| 1 | $9.9 \times 10^6$ | $1.5 \times 10^7$ | $1.9 \times 10^7$ | $5.3 \times 10^5$ | $3.8 \times 10^6$ |
| 2 | $2.0 \times 10^7$ | $1.7 \times 10^7$ | $3.2 \times 10^6$ | $6.8 \times 10^6$ | $6.0 \times 10^5$ |
| 3 | $4.1 \times 10^7$ | $5.3 \times 10^7$ | $2.4 \times 10^7$ | $2.6 \times 10^7$ | $9.9 \times 10^6$ |
| 4 | $3.2 \times 10^7$ | $1.5 \times 10^7$ | $1.7 \times 10^7$ | $2.6 \times 10^6$ | $1.0 \times 10^6$ |

EXAMPLE 6

Viability of the Probiotic in a Hydrophobic Component

The viability of the probiotic in a hydrophobic medium was tested. The hydrophobic medium was prepared according to the methodology of Example 1.

The results show that the *Bifidobacteria* cell count in the hydrophobic component is stable for six months.

TABLE 9 viability of Bifidobacteria in a continuous oil phase

| 9.7.04 (1 week) | 15.10.04 (3.5 months) | 05.11.04 (4 months) | 05.12.04 (5 months) | 05.01.05 (6 months) |
|---|---|---|---|---|
| $1.6 \times 10^{10}$ | $1.7 \times 10^{10}$ | $1.6 \times 10^{10}$ | $1.1 \times 10^{10}$ | $11.6 \times 10^{10}$ |

EXAMPLE 7

Viability of Probiotic in Water-in-Oil/Oil-in-Water Products

Samples 1 to 6 were formed using the compositions of table 10 (below) and the methodology of Example 2.

TABLE 10

Components of low fat water-in-oil/oil-in-water spreads

| Sample No. | 1 | 2 | 3 | 4 | 5 | 6 |
|---|---|---|---|---|---|---|
| Product Type | 20% Low fat W/O | 40% Low Fat W/O | 40% Low fat O/W | 40% Low fat O/W | 20% Low fat W/O | 20% Low fat W/O |
| Date | 19/10/04 | 19/10/04 | 19/10/04 | 19/10/04 | 11/02/04 | 11/02/04 |
| Batch size (g) | 4000 | 4000 | 6000 | 6000 | 4000 | 4000 |
| Water | 74 | 55.5 | 55.5 | 55.5 | 74 | 74 |
| Salt | 0.5 | 0.5 | 0.5 | 0.5 | 0.5 | 0.5 |
| Litesse ® II | 4 | 1.8 | 4 | | 1.8 | 4 |
| GRINDSTED LFS 560 | 1 | | | | 1 | 0.5 |
| GRINDSTED Pectin LA 410 | | 1 | | | | |
| GRINDSTED FF 1122 | | | 4 | 4 | | |
| Butter Milk Powder | 2 | 2 | 2 | | | |
| Bf. Species 420 | 0.04 | 0.04 | 0.04 | 0.04 | | |
| HOWARU Bifido | | | | | 0.04 | 0.04 |
| Potassium sorbate | 0.1 | 0.1 | 0.1 | 0.1 | 0.1 | 0.1 |
| EDTA | 0.015 | 0.015 | | | 0.015 | 0.015 |
| pH | 5.5 | 5.5 | 5 | 5 | 5.5 | 5.5 |
| PK4-INES | 20 | 30 | | | 20 | 20 |
| Liquid Oil | 80 | 70 | 100 | 100 | 80 | 80 |
| Fat in parts | 100 | 100 | 100 | 100 | 100 | 100 |
| FAT total | 17.46 | 38.16 | 33.86 | 39.86 | 21.56 | 19.86 |
| Dimodan U/J | 0.6 | 0.8 | | | 0.6 | 0.6 |
| GRINDSTED PGPR 90 PLUS | | | | | 0.4 | 0.4 |
| GRINDSTED PGPR 90 | 0.3 | 0.1 | | | | |
| PPMB β-carotene | 6 | 4 | 6 | 6 | 5 | 5 |
| RECEIPE total | 100 | 100 | 100 | 100 | 100 | 100 |
| Butter T13478 (o) | 0.04 | 0.02 | | 0.01 | | |
| Butter T03559 (o) | | | 0.01 | 0.02 | | |
| Yoghurt T02090 (w) | | | 0.02 | | | |

Using the compositions of table 10, prepared by a method according to the present invention, it was possible to obtain stable water-in-oil and oil-in-water products comprising viable lacetic acid bacteria which remain viable for prolonged periods of time, specifically the water-in-oil and oil-in-water products contain $10^6$ to $10^8$ CFU/g after 12 weeks.

TABLE 11

Viability of Bifidobacteria in the water-in-oil/oil-in-water product Cell counts [cfu/g]

| Sample | Bifidobacteria Fresh | Bifidobacteria DOM + 6 weeks | Bifidobacteria DOM + 12 weeks |
|---|---|---|---|
| 1a | $2 \times 10^8$ | $3.7 \times 10^7$ | $4.1 \times 10^7$ |
| 1b | | $8.8 \times 10^7$ | $3 \times 10^7$ |
| 2a | $2 \times 10^8$ | $3.1 \times 10^7$ | $2.3 \times 10^7$ |
| 2b | | $4.8 \times 10^7$ | $7.6 \times 10^7$ |
| 3a | $2.1 \times 10^8$ | $1.0 \times 10^8$ | $1.7 \times 10^7$ |
| 3b | | $1.9 \times 10^8$ | $1.6 \times 10^7$ |
| 4a | $8.7 \times 10^7$ | $1 \times 10^7$ | $4.5 \times 10^7$ |
| 4b | | $3.9 \times 10^7$ | $4 \times 10^7$ |
| 5 | $2.2 \times 10^7$ | $3.3 \times 10^7$ | $3.1 \times 10^7$ |
| 6 | $2 \times 10^8$ | $6.2 \times 10^7$ | $4 \times 10^7$ |

EXAMPLE 8

Viability of Probiotic in Peanut Butter

Samples 1 to 3 were formed by heating up refined peanut butter paste to 80° C. and adding other components such as sugar, salt and/or emulsifiers (see table 12 for the specific components added).

TABLE 12 composition of the peanut butter dispersions of samples 1 to 3

| Sample | 1 | 2 | 3 |
|---|---|---|---|
| Batch size (g) | 5000 | 5000 | 5000 |
| Sugar | 2 | 2 | |
| Salt | 1 | 0.5 | |
| Peanut butter paste | 95 | 96.5 | 98 |
| Dimodan MB 90 | | 0.5 | |
| GRINDSTED PGE O 70 | 0.3 | 0.3 | 0.3 |
| GRINDSTED PS 201 | 1.5 | | 1.5 |
| GRINDSTED Citrem 2-in-1 | 0.2 | 0.2 | 0.2 |
| Recipe total | 100 | 100 | 100 |

The paste is cooled in a SSHE to approximately 35° C., transferred to a koruma mixer and placed under vacuum for 3 minutes. Throughout the experiment the bottom agitator of the koruma mixer was disabled and the near wall agitator was set on a low RPM. To the peanut butter dispersion, *Bifidobacterium* sp. 420 in liquid oil is admixed such that the percentage weight of probiotic in the peanut butter is 0.04. The formed peanut butter product is placed under vacuum for one minute and then packed at 30° C. into 150 g units, with minimal headspace, and stored.

Table 13 shows the viability of samples 1 to 3 one month after the Date Of Manufacture. Sample 1a, 2a and 3a were stored at 5° C. and samples 1b, 2b and 3b were stored at 20-23° C.

TABLE 13 viability of probiotic (cfu/g) in peanut butter

| Sample | Bifidobacteria DOM + 10 days | Bifidobacteria DOM + 1 month |
|---|---|---|
| 1a | $2.7 \times 10^8$ | $2.2 \times 10^8$ |
| 1b | $2.2 \times 10^8$ | $2.9 \times 10^8$ |
| 2a | $1.9 \times 10^8$ | $2.2 \times 10^8$ |
| 2b | $1.6 \times 10^8$ | $2.2 \times 10^8$ |
| 3a | $3.0 \times 10^8$ | $2.5 \times 10^8$ |
| 3b | $3.0 \times 10^8$ | $2.6 \times 10^8$ |
| 4a | $2.4 \times 10^8$ | $2.5 \times 10^8$ |
| 4b | $2.6 \times 10^8$ | $2.9 \times 10^8$ |
| 5a | $1.1 \times 10^8$ | $8.7 \times 10^7$ |
| 5b | $9.9 \times 10^7$ | $4.7 \times 10^7$ |
| 6a | $2.7 \times 10^8$ | $2.2 \times 10^8$ |
| 6b | $2.5 \times 10^8$ | $1.4 \times 10^8$ |

As can be seen, the *Bifidobacterium* cell count in all samples are stable after one month storage for products stored at 5° C. and 20-23° C.

Summary

The present invention will now be described by way of numbered paragraphs.

1. A composition suitable for forming a water-in-oil preparation, the composition comprising a water-in-oil emulsion and a combination wherein the combination contains a viable lacetic acid micro-organism in a continuous oil phase.
2. A composition according to paragraph 1 wherein said water-in-oil emulsion is formed separately from the combination.
3. A composition according to paragraph 1 wherein the combination is formed in situ.
4. A composition according to paragraph 2 wherein said continuous oil phase comprises unsaturated liquid oil and a triglyceride, preferably wherein the triglyceride also comprises a monoester.
5. A composition according to paragraph 3, wherein said continuous oil phase contains unsaturated liquid oil in the range of from about 95% to 98% and triglyceride in the range of from about 2% to 5%, wherein the triglyceride comprises at least 10% monoester.
6. A composition according to paragraph 4 wherein said triglycerides have an iodine value of from about 2 to about 35.
7. A composition according to paragraph 5, wherein said triglycerides can be fully hydrogenated and/or non-hydrogenated and/or partially hydrogenated, preferably wherein said triglyceryde is fully hydrogenated.
8. A composition according to any one of the preceding paragraphs wherein the viable lacetic acid micro-organism is added to the continuous oil phase in a powder form.
9. A composition according to paragraph 8 wherein said viable lacetic acid micro-organism is a viable lacetic acid bacterium.
10. A composition according to paragraph 9 wherein said probiotic viable lacetic acid bacterium is selected from a group consisting of the genera *Lactococcus*, *Streptococcus*, *Pediococcus*, *Enterococcus*, *Leuconostoc*, *Carnobacterium*, *Propionibacterium*, *Bifidobacterium* and *Lactobacillus*.
11. A composition according to paragraph 10 wherein the viable lacetic acid micro-organism belongs to the genus *Bifidobacterium*.
12. A composition according to paragraph 11 wherein the viable lacetic acid micro-organism belongs to the species *Bifidobacterium* sp. 420.
13. A composition according to paragraph 10, wherein the viable lacetic acid micro-organism belongs to the genus *Lactobacillus*.
14. A composition according to paragraph 13, wherein the viable lacetic acid micro-organism belongs to the species *Lactobacillus acidophilus*.
15. A composition according to any one of the preceding paragraphs wherein the viable lacetic acid micro-organism is capable of imparting a nutritional and/or a health benefit.
16. A composition according to any of paragraphs 1-15 wherein the water-in-oil emulsion contains from about 5% to about 98% fat content.
17. A composition according to paragraph 16 wherein said water-in-oil emulsion comprises a polydextrose.
18. A composition according to paragraph 17 wherein said polydextrose is selected from the group consisting of Litesse™, pectin and maltodextrin.
19. A container comprising a combination as defined in one of paragraphs 1-18.
20. A container comprising a combination as defined in paragraph 19, wherein said container has thereon a label indicating use and/or approval for use to provide nutrition and improve the microbial balance of the gastrointestinal tract after consumption of a product containing said combination.
21. Use of a composition to prepare a water-in-oil preparation said composition comprising a water-in-oil emulsion and a combination wherein said combination contains a viable lacetic acid micro-organism in a continuous oil phase.
22. A water-in-oil product produced using the composition according to any one of paragraphs 1-18.
23. A water-in-oil product comprising a composition as defined in any one of paragraphs 1-18.
24. A water-in-oil product according to paragraph 23 wherein the water-in-oil preparation has a fat content in the range of from about 5% to about 98%.
25. A method for producing a water-in-oil preparation, said method comprising the step of:
   i) forming a water-in-oil emulsion,
   ii) adding a combination as defined in any one of paragraphs 1-18 to a water-in-oil emulsion,
   iii) mixing products of i) and ii) to form a water-in-oil preparation, and
   iv) optionally packaging the preparation,
wherein the packaged water-in-oil preparation is capable of imparting nutritional and/or health benefits on the consumer.
26. A method according to paragraph 25, wherein after adding the combination the water-in-oil preparation is not subjected to physical manipulations that are capable of causing cell damage.
27. A method according to paragraph 26 wherein the lacetic acid micro-organism remains viable in the water-in-oil preparation.

28. A water-in-oil product obtained by the method of any one of paragraphs 25-27.
29. A water-in-oil product according to paragraph 28 wherein the oil content of the water-in-oil product is in the range of from about 5% to about 98% wt.
30. A water-in-oil product according to paragraph 29 wherein the fat content of the product is less than 40% wt.
31. A water-in-oil product according to paragraph 29 wherein the product is a water-in-oil buffer or a water-in-oil margarine.
32. A water-in-oil product according to any one of paragraphs 28-31, comprising from $10^8$-$10^9$ cfu/g of viable lacetic acid micro-organisms on the day of production.
33. A water-in-oil product according to paragraph 32, comprising from about $10^4$-$10^6$ cfu/g from about 2 to about 12 weeks after the day of production.
34. A water-in-oil product according to any one of paragraphs 28-33, wherein the product is capable of imparting nutritional and/or health benefits on the consumer.
35. A water-in-oil product according to any one of paragraphs 28-34 wherein said product is capable of imparting a probiotic effect and/or a prebiotic effect and/or a symbiotic effect.
36. A container comprising a water-in-oil product, wherein said product is a product according to any one of paragraphs 28-35.
37. A container comprising a water-in-oil product, wherein said product is a product according to any one of paragraphs 28-35 and wherein said container has thereon a label indicating use and/or approval for use to improve the nutritional and microbial balance of the gastrointestinal tract after consumption of said product.
38. Use of a composition according to any one of paragraphs 1 to 18 a water-in-oil preparation according to any one of paragraphs 22-24, or a water-in-oil product according to any one of paragraphs 28-35 obtained by the method of any one of paragraphs 25-27 to impart a nutritional and/or a health benefit.
39. A process for in situ production of a combination comprising the steps of:
   i) providing a viable lacetic acid micro-organism,
   ii) providing a continuous oil phase comprising unsaturated liquid oil and triglycerides where the triglyceride also comprises a monoester, and
   iii) mixing the products of steps i) and ii) so as to produce a viable lacetic acid micro-organism in a continuous oil phase.
40. A process according to paragraph 39 wherein the lacetic acid bacterium is added to the continuous oil phase in a powder form.
41. A process according to paragraph 40 wherein the viable lacetic acid bacterium can be *Bifidobacterium* and/or *Lactobacillus*.
42. A water-in-oil product, a method, a process or a use substantially as described herein.

Each of the references, patent applications and patents mentioned in this document and any manufacturer's instructions or catalogues for any products cited or mentioned herein, is hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry and food science or related fields are intended to be within the scope of the claims.

The invention claimed is:

1. A method of producing a water-in-oil product, said method comprising the step of: admixing a hydrophobic component with a water-in-oil emulsion to form said water-in-oil product, wherein said hydrophobic component comprises a probiotic in a hydrophobic medium, wherein the hydrophobic component is a continuous oil phase formed by heating and cooling the continuous oil phase to form a crystal network within the continuous oil phase, and then admixing the cooled continuous oil phase with the probiotic to obtain a suspension of the probiotic.

2. A method according to claim 1, wherein the probiotic is a viable micro-organism selected from the group consisting of: *Lactococcus, Streptococcus, Pediococcus, Enterococcus, Leuconostoc, Carnobacterium, Propionibacterium, Lactobacillus* and *Bifidobacterium*.

3. A method according to claim 2, wherein said micro-organism is a *Bifidobacterium* and/or *Lactobacillus*.

4. A method according to claim 3, wherein said micro-organism is species *Bifidobacterium* sp. 420 and/or *Lactobacillus acidophilus*.

5. A method according to claim 1, wherein the probiotic is added to the hydrophobic medium in dry form.

6. A method according to claim 1, wherein after admixing the hydrophobic component the water-in-oil product is not subjected to physical manipulations that are capable of causing cell damage.

7. A method according to claim 1, wherein the water-in-oil product further comprises a prebiotic.

8. A method of preparing a probiotic product comprising: admixing a dispersion with an inert hydrophobic component wherein said hydrophobic component comprises a probiotic in a hydrophobic medium, such that the probiotic is kept discrete from said dispersion in the admixed product, wherein the hydrophobic medium is a continuous oil phase which is formed by heating and cooling the continuous oil phase to form a crystal network within the continuous oil phase, and then admixing the cooled continuous oil phase with the probiotic to obtain a suspension of the probiotic.

9. A method according to claim 8 wherein the dispersion is an emulsion.

10. A method according to claim 9 wherein the emulsion is a water-in-oil emulsion.

11. A method according to claim 8 wherein the probiotic product is peanut butter.

12. A product produced by the method of claim 8 or claim 10.

13. A product obtained by use of the product produced by the method of claim 1 or claim 8.

14. A product according to claim 12 when packaged.

15. A product according to claim 13 when packaged.

16. A method according to claim 1 or claim 8 wherein the continuous oil phase comprises unsaturated liquid oil and a triglyceride composition wherein the triglyceride composition further comprises a fatty acid monoester.

17. A method according to claim 1 or claim 8 wherein the continuous oil phase comprises unsaturated liquid oil and a triglyceride composition wherein the triglyceride composition further comprises a glycerol monoester.

18. A method according to claim 16 wherein the unsaturated liquid oil and the triglyceride are heated to a temperature in the range of from about 70° C. to about 85° C.

19. A method according to claim 18 wherein the unsaturated liquid oil and the triglyceride are heated to a temperature in the range of from about 75° C. to about 80° C.

20. A method according to claim 1 or claim 8 wherein the continuous oil phase is cooled to a temperature of about 20° C.

21. A method according to claim 20 wherein upon cooling, the continuous oil phase forms a gel.

22. A hydrophobic component comprising a continuous oil phase and a probiotic wherein the hydrophobic component is produced by heating and cooling the continuous oil phase to form a crystal network within the continuous oil phase, and then admixing the cooled continuous oil phase with the probiotic to obtain a suspension of the probiotic.

* * * * *